(12) United States Patent
Yao et al.

(10) Patent No.: US 8,304,610 B2
(45) Date of Patent: *Nov. 6, 2012

(54) BRASSICA JUNCEA LINES WITH HIGH OLEIC ACID PROFILE IN SEED OIL

(75) Inventors: Kening Yao, Saskatoon (CA); Derek A. Potts, Saskatoon (CA); Daryl Males, Saskatoon (CA)

(73) Assignee: Viterra, Inc., Regina, Saskatchewan (CA)

( * ) Notice: Subject to any disclaimer, the term of this patent is extended or adjusted under 35 U.S.C. 154(b) by 1078 days.

This patent is subject to a terminal disclaimer.

(21) Appl. No.: 12/036,710

(22) Filed: Feb. 25, 2008

(65) Prior Publication Data

US 2008/0168587 A1    Jul. 10, 2008

Related U.S. Application Data

(63) Continuation-in-part of application No. 10/895,520, filed on Jul. 20, 2004, now Pat. No. 7,423,198, which is a continuation-in-part of application No. 10/330,775, filed on Dec. 26, 2002, now Pat. No. 7,605,301.

(30) Foreign Application Priority Data

May 15, 2002 (CA) ..................... 2382767
Feb. 22, 2008 (CA) ..................... 2619858

(51) Int. Cl.
*A01H 5/00* (2006.01)
(52) U.S. Cl. ................................ 800/306; 800/270
(58) Field of Classification Search .................... None
See application file for complete search history.

(56) References Cited

U.S. PATENT DOCUMENTS

| | | | |
|---|---|---|---|
| 4,554,101 A | 11/1985 | Hopp | |
| 5,625,130 A | 4/1997 | Grant et al. | |
| 5,668,299 A | 9/1997 | DeBonte et al. | |
| 5,840,946 A | 11/1998 | Wong et al. | |
| 5,850,026 A | 12/1998 | DeBonte et al. | |
| 5,861,187 A | 1/1999 | DeBonte et al. | |
| 6,063,947 A | 5/2000 | Debonte et al. | |
| 6,084,157 A | 7/2000 | DeBonte et al. | |
| 6,303,849 B1 | 10/2001 | Potts et al. | |
| 6,723,895 B2 * | 4/2004 | DeBonte et al. | 800/281 |
| 6,787,686 B2 | 9/2004 | Potts et al. | |
| 7,423,198 B2 * | 9/2008 | Yao et al. | 800/306 |
| 7,605,301 B2 | 10/2009 | Yao et al. | |
| 2003/0221217 A1 | 11/2003 | Yao et al. | |

FOREIGN PATENT DOCUMENTS

| | | |
|---|---|---|
| AU | 2003204171 | 12/2003 |
| AU | 2004203364 | 2/2006 |
| AU | 2008202988 | 7/2008 |
| AU | 2008202989 | 7/2008 |
| AU | 2008200860 | 9/2009 |
| CA | 2226397 | 9/1999 |
| CA | 2382767 | 11/2003 |
| CA | 2471884 | 1/2006 |
| CA | 2619858 | 8/2009 |
| EP | 945 514 A1 | 9/1999 |
| WO | WO 94/11516 A1 | 5/1994 |
| WO | WO 96/27285 | 9/1996 |
| WO | WO 98/56239 A1 | 12/1998 |
| WO | WO 00/07433 A1 | 2/2000 |
| WO | WO 00/11012 A1 | 3/2000 |

OTHER PUBLICATIONS

US-7,605,301, Nov. 27, 2003, Yao, Kening, et al., Preliminary Amendment dated Dec. 26, 2002.
US-7,605,301, Nov. 27, 2003, Yao, Kening, et al., $2^{nd}$ Preliminary Amendment dated Mar. 4, 2003.
US-7,605,301, Nov. 27, 2003, Yao, Kening, et al., Restriction Requirement dated Sep. 23, 2005.
US-7,605,301, Nov. 27, 2003, Yao, Kening, et al., Response to Restriction Requirement of Sep. 23, 2005 dated Dec. 22, 2005.
US-7,605,301, Nov. 27, 2003, Yao, Kening, et al., Office Action dated Feb. 17, 2006.
US-7,605,301, Nov. 27, 2003, Yao, Kening, et al., Response to Office Action of Feb. 17, 2006 dated Aug. 17, 2006.
US-7,605,301, Nov. 27, 2003, Yao, Kening, et al., Office Action dated Oct. 30, 2006.
US-7,605,301, Nov. 27, 2003, Yao, Kening, et al., Response to Office Action of Oct. 30, 2006 dated Apr. 30, 2007.
US-7,605,301, Nov. 27, 2003, Yao, Kening, et al., Final Office Action dated Jul. 11, 2007.
US-7,605,301, Nov. 27, 2003, Yao, Kening, et al., Response to Final Office Action of Jul. 11, 2007 and RCE dated Nov. 8, 2007.
US-7,605,301, Nov. 27, 2003, Yao, Kening, et al., Final Office Action dated Feb. 20, 2008.
US-7,605,301, Nov. 27, 2003, Yao, Kening, et al., Response to Final Office Action of Feb. 20, 2008 dated Apr. 18, 2008.
US-7,605,301, Nov. 27, 2003, Yao, Kening, et al., Advisory Action dated May 13, 2008.

(Continued)

*Primary Examiner* — Elizabeth McElwain
(74) *Attorney, Agent, or Firm* — Jondle & Associates, P.C.

(57) ABSTRACT

In various aspects, the invention provides *Brassica juncea* plants, seeds, cells, nucleic acid sequences and oils. Edible oil derived from plants of the invention may have significantly higher oleic acid content than other *B. juncea* plants. In one embodiment, the *B. juncea* line MJ02-357-3 contains a mutant allele MJ02-313-1/BjFAD2-a at the BjFAD2-a gene locus, having a single base-pair change (a G to A substitution in the ORF at position 281 in reference to the first ATG start codon) relative to the wild type sequence. The change is predicted to encode a Glycine-94 Aspartic acid mutation in the sequence of the predicted BjFAD2-a protein. In another embodiment, the *B. juncea* line MJ02-357-3 contains a mutant allele MJ02-357-3/BjFAD2-a at the BjFAD2-a gene locus, having a single base-pair change (a C to T substitution in the ORF at position 647 in reference to the first ATG start codon) relative to the wild type sequence. The change is predicted to encode a Proline-216 Leucine mutation in the sequence of the predicted BjFAD2-a protein. As a result of these mutations, it can be predicted that the function of the BjFAD2-a proteins are negatively affected in *Brassica juncea* lines MJ02-313-1 and MJ357-3 as reflected in the increased levels of oleic acid in seed oil in comparison with the wild-type line J96D-4830. Seeds from MJ02-313-1 and MJ02-357-3 plants may for example yield an oil having oleic acid content of greater than 70% by weight.

12 Claims, 9 Drawing Sheets

OTHER PUBLICATIONS

US-7,605,301, Nov. 27, 2003, Yao, Kening, et al., Response to Advisory Action of May 13, 2008 dated Jun. 19, 2008.
US-7,605,301, Nov. 27, 2003, Yao, Kening, et al., Advisory Action dated Jul. 18, 2008.
US-7,605,301, Nov. 27, 2003, Yao, Kening, et al., Response to Advisory Action of Jul. 18, 2008 and RCE dated Aug. 15, 2008.
US-7,605,301, Nov. 27, 2003, Yao, Kening, et al., Office Action dated Nov. 26, 2008.
US-7,605,301, Nov. 27, 2003, Yao, Kening, et al., Response to Office Action of Nov. 26, 2008 dated Feb. 24, 2009.
US-7,605,301, Nov. 27, 2003, Yao, Kening, et al., Notice of Allowance dated Jun. 10, 2009.
US-7,423,198, Feb. 17, 2005, Yao, Kening, et al., Preliminary Amendment dated Oct. 18, 2004.
US-7,423,198, Feb. 17, 2005, Yao, Kening, et al., Restriction Requirement dated Jan. 19, 2007.
US-7,423,198, Feb. 17, 2005, Yao, Kening, et al., Response to Restriction Requirement of Jan. 9, 2007 dated Mar. 9, 2007.
US-7,7,423,198, Feb. 17, 2005, Yao, Kening, et al., Office Action dated May 31, 2007.
US-7,7,423,198, Feb. 17, 2005, Yao, Kening, et al., Response to Office Action of May 31, 2007 and Supplemental Amendment dated Nov. 29, 2007.
US-7,7,423,198, Feb. 17, 2005, Yao, Kening, et al., Notice Re Non-Compliant or Non-Responsive Amendment dated Dec. 14, 2007.
US-7,7,423,198, Feb. 17, 2005, Yao, Kening, et al., Response to Notice Re Non-Compliant or Non-Responsive Amendment of Dec. 14, 2007 dated Dec. 28, 2007.
US-7,7,423,198, Feb. 17, 2005, Yao, Kening, et al., Exaiminer-Initiated Interview Summary dated Apr. 10, 2008.
US-7,7,423,198, Feb. 17, 2005, Yao, Kening, et al., Notice of Allowance dated Apr. 21, 2008.
AU 2003204171, Dec. 4, 2003, Viterra Inc., Examiner's Report dated Mar. 22, 2007.
AU 2003204171, Dec. 4, 2003, Viterra Inc., Response to Examiner's Report of Mar. 22, 2007 dated Mar. 19, 2008.
AU 2003204171, Dec. 4, 2003, Viterra Inc., Notice of Acceptance dated Mar. 28, 2008.
AU 2004203364, Feb. 9, 2006, Viterra Inc., Examiner's Report dated Jun. 29, 2009.
AU 2008202988, Jul. 31, 2008, Viterra Inc., Preliminary Amendment dated Jul. 24, 2008.
AU 2008202989, Jul. 31, 2008, Viterra Inc., Preliminary Amendment dated Jul. 24, 2008.
CA 2,382,767, Nov. 15, 2003, Viterra Inc., Voluntary Amendment dated May 22, 2002.
CA 2,382,767, Nov. 15, 2003, Viterra Inc., Courtesy Letter dated Jun. 11, 2002.
CA 2,382,767, Nov. 15, 2003, Viterra Inc., Response to Courtesy Letter of Jun. 11, 2002 dated Jul. 16, 2002.
CA 2,382,767, Nov. 15, 2003, Viterra Inc., Office Action dated Jun. 12, 2007.
CA 2,382,767, Nov. 15, 2003, Viterra Inc., Notice of Abandonment dated Mar. 5, 2008.
CA 2,382,767, Nov. 15, 2003, Viterra Inc., Request for Reinstatement and Response to Office Action of Jun. 12, 2007 dated Dec. 5, 2008.
CA 2,382,767, Nov. 15, 2003, Viterra Inc., Office Action dated Jun. 5, 2010.
CA 2,471,884, Jan. 15, 2006, Viterra Inc., Courtesy Letter dated Aug. 10, 2004.
CA 2,471,884, Jan. 15, 2006, Viterra Inc., Response to Courtesy Letter of Aug. 10, 2004 dated Aug. 20, 2004.
Kim, et al. 1994, Plant Molecular Biology 24: 105-117.
Singh, Genbank Acc. No. X91139 (Dec. 24, 2000).
Sivaraman, Genbank Acc. No. AJ459108 (May 9, 2002).
Agnihotri, A., Kaushik, N., Singh, N. K., Raney, J.P. and Downey, R. K. 1995. Selection for better agrononical and nutritional characteristics in Indian rapeseed-mustard. Proc. 9.sup.th Int. Rapeseed Cong., Cambridge, U.K. vol. 2:425-427.
Altschul et al., 1990, J. Mol. Biol. 215:403-10.
Ames, B. N. 1983. Dietary carcinogens and anticarcinogens. Science 221:1256-1264.

Ausubel, et al., (eds), 1989, Current Protocols in Molecular Biology, vol. 1, Green Publishing Associates, Inc., and John Wiley & Sons, Inc., New York, at p. 2.10.3 (4 pages).
Daun, J. K. and McGregor, D. I. 1991. Glucosinolates in seeds and residues. In: Analysis of Oilseeds, Fats and Fatty foods. J. B. Rossell and J. L. R. Pritchard, eds. Elsevier Applied Science, London, pp. 185-226.
Downey, R. K. and Rakow, G. F. W. 1987. Rapeseed and mustard. In: Principles of cultivar development. W. R. Fehr, ed. Macmillian, N. Y. Chapt. 12, pp. 437-486.
Eskin, N. A. M., Vaisey-Genser, M., Durance-Todd, S. and Przybylski, R. 1989. Stability of low linolenic acid canola oil to frying temperatures. J. Amer. Oil Chem. Soc. 66: 1081-1084.
Food Chemicals Codex. 1996. 4.sup. th Edition. Committee on Food Chemicals Codex, Food and Nutrition Board, Institute of Medicine, National Academy of Sciences. National Academy Press, Washington. pp. 77-79.
Griffiths et al., Biochem. J. 252: 641-647, 1988.
Henikoff and Henikoff, 1992, Proc. Natl. Acad. Sci. USA 89: 10915-10919.
Jeong et al., Proceedings of the 3rd National Plant Lipid Cooperative Meeting, 1999, California. Molecular Characterization of A High Oleate Trait and Its Inheritance Pattern in the Cultivated Peanut (*Arachis hypogaea* L.).
Kirk, J. T. O. and Oram, R. N. 1981. Isolation of erucic acid free lines of *Brassica juncea*: Indian mustard now a potential oilseed crop in Australia. J. Aust. Inst. Agric. Sci. 47:51-52.
Hammond, E. G. et al., "Improving the Fatty Acid Composition of Soybean Oil", JAOCS, vol. 61, No. 11 (Nov. 1984).
Love, H. K., Rakow, G., Raney, J. P. and Downey, R. K. 1990. Development of low glucosinolate mustard. Can. J. Plant Sci. 70:419-424.
Love, H. K., Rakow, G., Raney, J. P. and Downey, R. K. 1991. Breeding improvements towards canola quality *Brassica juncea*. Proc. 8.sup.th Int. Rapeseed Congress, Saskatoon, Canada. vol. 1:164-169.
Marillia and Taylor, Plant Physiol. 120: 339, 1999.
McDonald, B. E. 1995. Oil properties of importance in human nutrition. In: *Brassica* Oilseeds: Production and Utilization. D. S. Kimber and D. I. McGregor, eds., CAB International, Oxon, U.K., pp. 291-299.
Miquel and Browse, J. Bio. Chem. 267: 1502-1509, 1992.
Napoli et al., 1990 Plant Cell 2: 279-289.
Needleman and Wunsch, 1970, J. Mol. Biol. 48:443.
Okuley et al., Plant Cell 6: 147-158, 1994.
Pearson and Lipman, 1988, Proc. Natl. Acad. Sci. USA 85: 2444.
Potts and Males. 1999. Inheritance of fatty acid composition in *Brassica juncea*. The proceedings of 10th International Rapeseed Congress in Sep. 26-29, 1999; Canberra, Australia; CD-ROM.
Poehlman, John M. et al., (4th ed. 1995). Breeding Field Crops, Chpt. III. Tools of the Plant Breeder, Iowa State Univ. Press, Ames, Iowa, pp. 108-109.
Potts et al., 1999. Canola-quality *Brassica juncea*, a new oilseed crop for the Canadian prairies. The proceedings of 10th International Rapeseed Congress in Sep. 26-29, 1999; Canberra, Australia; CD-ROM.
Rakow, G. 1991. Canola quality mustard. Proc. Special Cropportunities I: A conference organized by the Crop Development Centre and the Extension Division, University of Saskatchewan, Saskatoon, Canada pp. 55-59.
Rakow, G., Raney, J. P. and Males, D. 1995. Field performance of canola quality *Brassica juncea* Proc. 9.sup.th Int. Rapeseed Congress, Cambridge, U.K. vol. 2:428-430.
Raney, P., Rakow, G. and Olson, T. 1995. Development of zero erucic, low linolenic *Brassica juncea* utilizing interspecific crossing. Proc. 9.sup.th Int. Rapeseed Congress, Cambridge, U.K. vol. 2:413-415.
Shanklin and Somerville, Proc. Natl. Acad. Sci. USA 88: 2510-2514, 1991.
Shanklin et al., Biochemistry 33: 12787-12794, 1994.
Singh et al., 1995. Plant Physiol. 109: 1498.
Smith, Temple. F., et al., "Comparison of Biosequences", Advances in Applied Mathematics 2: 482-489 (1981).

Stotjesdijk et al., 1999. Genetic manipulation for altered oil quality in *Brassica*. The proceedings of 10th International Rapeseed Congress in Sep. 26-29, 1999; Canberra, Australia; CD-ROM.

Swanson, E. B., Coumans, M. P., Brown, G. L., Patel, J. D. and Beversdorf, W. D. 1988. The characterization of herbicide tolerant plants in *Brassica napus* L. after in vitro selectino of microspores and protoplasts. Plant Cell Rep. 7:83-87.

Swanson, E. B., Herrgesell, M. J., Arnoldo, M., Sippell, D. W. and Wong, R. S. C. 1989. Microspore mutagenesis and selection: canola plants with field tolerance to the imidazolinones. Theor. Appl. Genet. 78:525-530.

Tanhuanpaa et al., Mol. Breed. 4: 543-550, 1998.

Thiagarajah, M. R. and Stringham, G. R. 1993. A comparison of genetic segregation in traditional and microspore-derived population of *Brassica juncea* L. Czern and Coss. Plant Breeding 111:330-334.

Tijssen, "Overview of principles of hybridization and the strategy of nucleic acid probe assays", Laboratory Techniques in Biochemistry and Molecular Biology—Hybridization with Nucleic Acid Probes, pp. 19-78 (1993).

Dellaporta, Stephen, L. et al., "A Plant DNA Minipreparation: Version II", Plant Molecular Biology Reporter 1:19-21 (1983).

Woods, D. L., Capcara, J. J. and Downey, R. K. 1991. The potential of mustard (*Brassica juncea* (L.) Coss) as an edible oil crop on the Canadian Prairies. Can. J. Plant Sci. 71:195-198.

Zhu et al., 1999. Proc. Natl. Acad. Sci. 96:8768-8773.

Zhu et al., 2000. Nature Biotechnology 18: 555-558.

CA 2,382,767, Nov. 15, 2003, Viterra Inc., Response to Office Action of Jan. 5, 2010 dated Jul. 5, 2010.

Australian Application No. 2008202988, Examiner's Report dated Dec. 17, 2010, 3 pages.

Australian Application No. 2008202989, Examiner's Report dated Dec. 17, 2010, 3 pages.

Canadian Application No. 2,471,884, Examiner's Report dated Feb. 7, 2011, 3 pages.

Australian Aplpication No. 2004203364, Examiner's Report dated Feb. 15, 2011, 2 pages.

Australian Application No. 2004203364, Notice of Acceptance dated Mar. 22, 2011, 2 pages.

GenBank Accession AF124360, "*Brassica carinata* delta-12 desaturase (FAD2) mRNA, complete cds", Jul. 21, 2000, 1 page.

Sivaraman, I., et al., "Development of high oleic and low linoleic acid transgenics in a zero erucic acid *Brassica juncea* L. (Indian mustard) line by antisense suppression of the *fad2* gene", Molecular Breeding, vol. 13, May 2004, pp. 365-375.

* cited by examiner

FIGURE 2

```
gatatttttt taagtttttt tctcacatgg gagaagaaga agccaagcac   50
gatcctccat tctcaacttt atagcatttt tttctttttct ttccggctac  100
cactaacttc tacagttcta cttgtgagtc ggcaaggacg tttcctcata  150
ttaaagtaaa gacatcaaat accataatct taatgctaat taacgtaacg  200
gatgagttct ataacacaac ccaaactagt ctttgtgaac attaggattg  250
ggtaaaccaa tatttacatt ttaaaaacaa aatacaaaaa gaaacgtgat  300
aaactttata aaagcaatta tatgatcacg gcatctttt  cacttttccg  350
taaatatata aagtggtgt  aaatatcaga tatttggagt agaaaaaaaa  400
aaaaaaaaaa agaaatatga agagaggaaa taatggaggg gcccactagt  450
aaaaagaaa  gaaagagat  gtcactcaat cgtctcacac gggcccccgt   500
caatttaaac ggcctgcctt ctgcccaatc gcatcttacc agaaccagag   550
agattcatta ccaaagagat agagagagaa agagaggaga cagagagagt  600
ttgaggaggt gcttcttcgt agggttcatc gttattaacg ttaaatcttc   650
atcccccctac gtcaaccagc tcaaggtccc tttcttcttc catttcctct  700
cattttacg  ttgttttcaa tcttggtctg ttctttcct  atcgcttttc   750
tattctatct atcattttg  cttttcagtc gatttaattc tagacctgtt   800
aatatttatt gcattaaact atagatctgt tcttgattct ctgttttctt   850
gtgtgaaatc ttgatgctgt ctttaccatt aatctgatta tattgtctat  900
accttggaga atatgaaatg ttgcattttc atttgtccga atacaaactg  950
tttgactttc aatcttttt  aatgatttat tttgatgggt tggtggagtt 1000
gaaaaatcac catagcagtc tcacgtcctg gtcttagaaa tatccttcct 1050
attcaaagtt atatata ttt gtttacttgt cttagatctg gacctgagac 1100
atgtaagtac ctatttgttg aatctttggg taaaaaactt atgtctctgg 1150
gtaaaatttg cttggagatt tgaccgattc ctattggctc ttgattctgt 1200
aattacgtaa tacatgaaaa atgtttcatt tggcctatgc tcacttcatg 1250
cttataaact ttttcttgca aattaattgg attagatgct ccttcataga 1300
ttcagatgca atagatttgc atgaagaaaa taatagaatt catgatagta 1350
aaaagattgt attttttgttt gtttgtttat gtttaaaagt ctatatgttg 1400
acaatagagt tgctatcaac tgtttcattt aggtttatgt ttttgtcaag 1450
ttgcttattc taagagacat tgtgattatg acttgtcttc tctaacgtag 1500
tttagtaata aaagacgaaa gaattgata  tccacaagaa agagatgtaa 1550
gctgtaacgt atcaaatctc attaataact agtagtattc tcaacgctat 1600
cgtttatttc tttctttggt ttgccactat atgccgcttc tctcctcttt 1650
tgtcccacgt actatccatt tttttgaaac tttaataacg taacactgaa 1700
tattaatttg ttggtttaat taactttgag tttgttttg  gtttatgcag 1750
aaacATGGGT GCAGGTGGAA GAATGCAAGT GTCTCCTCCC TCGAAGAAGT 1800
CTGAAACCGA CACCATCAAG CGCGTACCCT GCGAGACACC GCCCTTCACT 1850
GTCGGAGAAC TCAAGAAAGC AATCCCACCG CACTGTTTCA AACGCTCGAT 1900
CCCTCGCTCT TTCTCCTACC TCATCTGGGA CATCATCATA GCCTCCTGCT 1950
```

```
TCTACTACGT CGCCACCACT TACTTCCCTC TCCTCCCTCA CCCTCTCTCC 2000
TACTTCGCCT GGCCTCTCTA CTGGGCCTGC CAGGGCTGCG TCCTAACCGG 2050
CGTCTGGGTC ATAGCCCACG AGTGCGGCCA CCACGCCTTC AGCGACTACC 2100
AGTGGCTTGA CGACACCGTC GGTCTCATCT TCCACTCCTT CCTCCTCGTC 2150
CCTTACTTCT CCTGGAAGTA CAGTCATCGA CGCCACCATT CCAACACTGG 2200
CTCCCTCGAG AGAGACGAAG TGTTTGTCCC CAAGAAGAAG TCAGACATCA 2250
AGTGGTACGG CAAGTACCTC AACAACCCTT TGGGACGCAC CGTGATGTTA 2300
ACGGTTCAGT TCACTCTCGG CTGGCCTTTG TACTTAGCCT TCAACGTCTC 2350
GGGAAGACCT TACGACGGCG GCTTCGCTTG CCATTTCCAC CCTAACGCTC 2400
CCATCTACAA CGACCGCGAG CGTCTCCAGA TATACATCTC CGACGCTGGC 2450
ATCCTCGCCG TCTGCTACGG TCTCTACCGC TACGCTGCTG TCCAAGGAGT 2500
TGCCTCGATG GTCTGCTTCT ACGGAGTCCC GCTTCTGATA GTCAACGGGT 2550
TCTTAGTTTT GATCACTTAC TTGCAGCACA CGCATCCTTC CCTGCCTCAC 2600
TACGATTCGT CTGAGTGGGA TTGGTTGAGG GGAGCGTTGG CTACCGTTGA 2650
CAGAGACTAC GGGATCTTGA CAAGGTCTT CCACAATATC ACGGACACGC 2700
ACGTGGCGCA TCACCTGTTC TCGACCATGC CGCATTATCA CGCGATGGAA 2750
GCTACCAAGG CGATAAAGCC GATACTGGGA GAGTATTATC AGTTCGATGG 2800
GACGCCGGTG GTTAAGGCGA TGTGGAGGGA GGCGAAGGAG TGTATCTATG 2850
TGGAACCGGA CAGGCAAGGT GAGAAGAAAG GTGTGTTCTG GTACAACAAT 2900
AAGTTATGA 2909                                   SEQ ID NO:1
```

```
gatattttt  taagttttt  tctcacatgg  gagaagaaga  agccaagcac    50
gatcctccat  tctcaacttt  atagcatttt  tttcttttct  ttccggctac   100
cactaacttc  tacagttcta  cttgtgagtc  ggcaaggacg  tttcctcata   150
ttaaagtaaa  gacatcaaat  accataatct  taatgctaat  taacgtaacg   200
gatgagttct  ataacacaac  ccaaactagt  ctttgtgaac  attaggattg   250
ggtaaaccaa  tatttacatt  ttaaaaacaa  aatacaaaaa  gaaacgtgat   300
aaactttata  aaagcaatta  tatgatcacg  gcatctttt   cacttttccg   350
taaatatata  taagtggtgt  aaatatcaga  tatttggagt  agaaaaaaaa   400
aaaaaaaaaa  agaaatatga  agagaggaaa  taatggaggg  gcccactagt   450
aaaaagaaa   gaaagagat   gtcactcaat  cgtctcacac  gggcccccgt   500
caatttaaac  ggcctgcctt  ctgcccaatc  gcatcttacc  agaaccagag   550
agattcatta  ccaaagagat  agagagagaa  agagaggaga  cagagagagt   600
ttgaggaggt  gcttcttcgt  agggttcatc  gttattaacg  ttaaatcttc   650
atccccctac  gtcaaccagc  tcaaggtccc  tttcttcttc  catttcctct   700
cattttacg   ttgttttcaa  tcttggtctg  ttcttttctt  atcgcttttc   750
tattctatct  atcattttg   cttttcagtc  gatttaattc  tagacctgtt   800
aatatttatt  gcattaaact  atagatctgt  tcttgattct  ctgttttctt   850
gtgtgaaatc  ttgatgctgt  ctttaccatt  aatctgatta  tattgtctat   900
accttggaga  atatgaaatg  ttgcatttc   atttgtccga  atacaaactg   950
tttgactttc  aatctttttt  aatgatttat  tttgatgggt  tggtggagtt  1000
gaaaaatcac  catagcagtc  tcacgtcctg  gtcttagaaa  tatccttcct  1050
attcaaagtt atatata ttt  gtttacttgt  cttagatctg  gacctgagac  1100
atgtaagtac  ctatttgttg  aatctttggg  taaaaaactt  atgtctctgg  1150
gtaaaatttg  cttggagatt  tgaccgattc  ctattggctc  ttgattctgt  1200
aattacgtaa  tacatgaaaa  atgtttcatt  tggcctatgc  tcacttcatg  1250
cttataaact  ttttcttgca  aattaattgg  attagatgct  ccttcataga  1300
ttcagatgca  atagatttgc  atgaagaaaa  taatagaatt  catgatagta  1350
aaaagattgt  atttttgttt  gtttgtttat  gtttaaaagt  ctatatgttg  1400
acaatagagt  tgctatcaac  tgtttcattt  aggtttatgt  ttttgtcaag  1450
ttgcttattc  taagagacat  tgtgattatg  acttgtcttc  tctaacgtag  1500
tttagtaata  aaagacgaaa  gaaattgata  tccacaagaa  agagatgtaa  1550
gctgtaacgt  atcaaatctc  attaataact  agtagtattc  tcaacgctat  1600
cgtttatttc  tttctttggt  ttgccactat  atgccgcttc  tctcctcttt  1650
tgtcccacgt  actatccatt  tttttgaaac  tttaataacg  taacactgaa  1700
tattaatttg  ttggtttaat  taactttgag  tttgtttttg  gtttatgcag  1750
aaacATGGGT  GCAGGTGGAA  GAATGCAAGT  GTCTCCTCCC  TCGAAGAAGT  1800
CTGAAACCGA  CACCATCAAG  CGCGTACCCT  GCGAGACACC  GCCCTTCACT  1850
GTCGGAGAAC  TCAAGAAAGC  AATCCCACCG  CACTGTTTCA  AACGCTCGAT  1900
CCCTCGCTCT  TTCTCCTACC  TCATCTGGGA  CATCATCATA  GCCTCCTGCT  1950
```

```
TCTACTACGT CGCCACCACT TACTTCCCTC TCCTCCCTCA CCCTCTCTCC 2000
TACTTCGCCT GGCCTCTCTA CTGGGCCTGC CAGGACTGCG TCCTAACCGG 2050
CGTCTGGGTC ATAGCCCACG AGTGCGGCCA CCACGCCTTC AGCGACTACC 2100
AGTGGCTTGA CGACACCGTC GGTCTCATCT TCCACTCCTT CCTCCTCGTC 2150
CCTTACTTCT CCTGGAAGTA CAGTCATCGA CGCCACCATT CCAACACTGG 2200
CTCCCTCGAG AGAGACGAAG TGTTTGTCCC CAAGAAGAAG TCAGACATCA 2250
AGTGGTACGG CAAGTACCTC AACAACCCTT TGGGACGCAC CGTGATGTTA 2300
ACGGTTCAGT TCACTCTCGG CTGGCCTTTG TACTTAGCCT TCAACGTCTC 2350
GGGAAGACCT TACGACGGCG GCTTCGCTTG CCATTTCCAC CCTAACGCTC 2400
CCATCTACAA CGACCGCGAG CGTCTCCAGA TATACATCTC CGACGCTGGC 2450
ATCCTCGCCG TCTGCTACGG TCTCTACCGC TACGCTGCTG TCCAAGGAGT 2500
TGCCTCGATG GTCTGCTTCT ACGGAGTCCC GCTTCTGATA GTCAACGGGT 2550
TCTTAGTTTT GATCACTTAC TTGCAGCACA CGCATCCTTC CCTGCCTCAC 2600
TACGATTCGT CTGAGTGGGA TTGGTTGAGG GGAGCGTTGG CTACCGTTGA 2650
CAGAGACTAC GGGATCTTGA ACAAGGTCTT CCACAATATC ACGGACACGC 2700
ACGTGGCGCA TCACCTGTTC TCGACCATGC CGCATTATCA CGCGATGGAA 2750
GCTACCAAGG CGATAAAGCC GATACTGGGA GAGTATTATC AGTTCGATGG 2800
GACGCCGGTG GTTAAGGCGA TGTGGAGGGA GGCGAAGGAG TGTATCTATG 2850
TGGAACCGGA CAGGCAAGGT GAGAAGAAAG GTGTGTTCTG GTACAACAAT 2900
AAGTTATGA        2909                             SEQ ID NO:2
```

```
gatattttt  taagttttt  tctcacatgg  gagaagaaga  agccaagcac    50
gatcctccat  tctcaacttt  atagcatttt  tttcttttct  ttccggctac   100
cactaacttc  tacagttcta  cttgtgagtc  ggcaaggacg  tttcctcata   150
ttaaagtaaa  gacatcaaat  accataatct  taatgctaat  taacgtaacg   200
gatgagttct  ataacacaac  ccaaactagt  ctttgtgaac  attaggattg   250
ggtaaaccaa  tatttacatt  ttaaaaacaa  aatacaaaaa  gaaacgtgat   300
aaactttata  aaagcaatta  tatgatcacg  gcatctttt   cacttttccg   350
taaatatata  taagtggtgt  aaatatcaga  tatttggagt  agaaaaaaaa   400
aaaaaaaaaa  agaaatatga  agagaggaaa  taatggaggg  gcccactagt   450
aaaaaagaaa  gaaaagagat  gtcactcaat  cgtctcacac  gggcccccgt   500
caatttaaac  ggcctgcctt  ctgcccaatc  gcatcttacc  agaaccagag   550
agattcatta  ccaaagagat  agagagagaa  agagaggaga  cagagagagt   600
ttgaggaggt  gcttcttcgt  agggttcatc  gttattaacg  ttaaatcttc   650
atccccctac  gtcaaccagc  tcaaggtccc  tttcttcttc  catttcctct   700
cattttacg   ttgttttcaa  tcttggtctg  ttcttttctt  atcgcttttc   750
tattctatct  atcatttttg  cttttcagtc  gatttaattc  tagacctgtt   800
aatatttatt  gcattaaact  atagatctgt  tcttgattct  ctgttttctt   850
gtgtgaaatc  ttgatgctgt  ctttaccatt  aatctgatta  tattgtctat   900
accttggaga  atatgaaatg  ttgcattttc  atttgtccga  atacaaactg   950
tttgactttc  aatcttttt   aatgatttat  tttgatgggt  tggtggagtt  1000
gaaaaatcac  catagcagtc  tcacgtcctg  gtcttagaaa  tatccttcct  1050
attcaaagtt atatata ttt  gtttacttgt  cttagatctg  gacctgagac  1100
atgtaagtac  ctatttgttg  aatctttggg  taaaaaactt  atgtctctgg  1150
gtaaaatttg  cttggagatt  tgaccgattc  ctattggctc  ttgattctgt  1200
aattacgtaa  tacatgaaaa  atgtttcatt  tggcctatgc  tcacttcatg  1250
cttataaact  ttttcttgca  aattaattgg  attagatgct  ccttcataga  1300
ttcagatgca  atagatttgc  atgaagaaaa  taatagaatt  catgatagta  1350
aaaagattgt  attttttgttt  gtttgtttat  gtttaaaagt  ctatatgttg  1400
acaatagagt  tgctatcaac  tgtttcattt  aggtttatgt  ttttgtcaag  1450
ttgcttattc  taagagacat  tgtgattatg  acttgtcttc  tctaacgtag  1500
tttagtaata  aaagacgaaa  gaaattgata  tccacaagaa  agagatgtaa  1550
gctgtaacgt  atcaaatctc  attaataact  agtagtattc  tcaacgctat  1600
cgtttatttc  tttctttggt  ttgccactat  atgccgcttc  tctcctcttt  1650
tgtcccacgt  actatccatt  ttttgaaac   tttaataacg  taacactgaa  1700
tattaatttg  ttggtttaat  taactttgag  tttgttttg   gtttatgcag  1750
aaacATGGGT  GCAGGTGGAA  GAATGCAAGT  GTCTCCTCCC  TCGAAGAAGT  1800
CTGAAACCGA  CACCATCAAG  CGCGTACCCT  GCGAGACACC  GCCCTTCACT  1850
GTCGGAGAAC  TCAAGAAAGC  AATCCCACCG  CACTGTTTCA  AACGCTCGAT  1900
CCCTCGCTCT  TTCTCCTACC  TCATCTGGGA  CATCATCATA  GCCTCCTGCT  1950
```

```
TCTACTACGT CGCCACCACT TACTTCCCTC TCCTCCCTCA CCCTCTCTCC 2000
TACTTCGCCT GGCCTCTCTA CTGGGCCTGC CAGGGCTGCG TCCTAACCGG 2050
CGTCTGGGTC ATAGCCCACG AGTGCGGCCA CCACGCCTTC AGCGACTACC 2100
AGTGGCTTGA CGACACCGTC GGTCTCATCT TCCACTCCTT CCTCCTCGTC 2150
CCTTACTTCT CCTGGAAGTA CAGTCATCGA CGCCACCATT CCAACACTGG 2200
CTCCCTCGAG AGAGACGAAG TGTTTGTCCC CAAGAAGAAG TCAGACATCA 2250
AGTGGTACGG CAAGTACCTC AACAACCCTT TGGGACGCAC CGTGATGTTA 2300
ACGGTTCAGT TCACTCTCGG CTGGCCTTTG TACTTAGCCT TCAACGTCTC 2350
GGGAAGACCT TACGACGGCG GCTTCGCTTG CCATTTCCAC CCTAACGCTC 2400
TCATCTACAA CGACCGCGAG CGTCTCCAGA TATACATCTC CGACGCTGGC 2450
ATCCTCGCCG TCTGCTACGG TCTCTACCGC TACGCTGCTG TCCAAGGAGT 2500
TGCCTCGATG GTCTGCTTCT ACGGAGTCCC GCTTCTGATA GTCAACGGGT 2550
TCTTAGTTTT GATCACTTAC TTGCAGCACA CGCATCCTTC CCTGCCTCAC 2600
TACGATTCGT CTGAGTGGGA TTGGTTGAGG GGAGCGTTGG CTACCGTTGA 2650
CAGAGACTAC GGGATCTTGA ACAAGGTCTT CCACAATATC ACGGACACGC 2700
ACGTGGCGCA TCACCTGTTC TCGACCATGC CGCATTATCA CGCGATGGAA 2750
GCTACCAAGG CGATAAAGCC GATACTGGGA GAGTATTATC AGTTCGATGG 2800
GACGCCGGTG GTTAAGGCGA TGTGGAGGGA GGCGAAGGAG TGTATCTATG 2850
TGGAACCGGA CAGGCAAGGT GAGAAGAAAG GTGTGTTCTG GTACAACAAT 2900
AAGTTATGA        2909                                 SEQ ID NO:3
```

```
J96D-4830    MGAGGRMQVS  PPSKKSETDT  IKRVPCETPP  FTVGELKKAI   40
MJ02-086-3   MGAGGRMQVS  PPSKKSETDT  IKRVPCETPP  FTVGELKKAI   40
MJ02-313-1   MGAGGRMQVS  PPSKKSETDT  IKRVPCETPP  FTVGELKKAI   40
MJ02-357-3   MGAGGRMQVS  PPSKKSETDT  IKRVPCETPP  FTVGELKKAI   40

J96D-4830    PPHCFKRSIP  RSFSYLIWDI  IIASCFYYVA  TTYFPLLPHP   80
MJ02-086-3   PPHCFKRSIP  RSFSYLIWDI  IIASCFYYVA  TTYFPLLPHP   80
MJ02-313-1   PPHCFKRSIP  RSFSYLIWDI  IIASCFYYVA  TTYFPLLPHP   80
MJ02-357-3   PPHCFKRSIP  RSFSYLIWDI  IIASCFYYVA  TTYFPLLPHP   80

J96D-4830    LSYFAWPLYW  ACQGCVLTGV  WVIAHECGHH  AFSDYQWLDD  120
MJ02-086-3   LSYFAWPLYW  ACQGCVLTGV  *VIAHECGHH  AFSDYQWLDD  120
MJ02-313-1   LSYFAWPLYW  ACQDCVLTGV  WVIAHECGHH  AFSDYQWLDD  120
J96D-357-3   LSYFAWPLYW  ACQGCVLTGV  WVIAHECGHH  AFSDYQWLDD  120

J96D-4830    TVGLIFHSFL  LVPYFSWKYS  HRRHHSNTGS  LERDEVFVPK  160
MJ02-086-3   TVGLIFHSFL  LVPYFSWKYS  HRRHHSNTGS  LERDEVFVPK  160
MJ02-313-1   TVGLIFHSFL  LVPYFSWKYS  HRRHHSNTGS  LERDEVFVPK  160
MJ02-357-3   TVGLIFHSFL  LVPYFSWKYS  HRRHHSNTGS  LERDEVFVPK  160

J96D-4830    KKSDIKWYGK  YLNNPLGRTV  MLTVQFTLGW  PLYLAFNVSG  200
MJ02-086-3   KKSDIKWYGK  YLNNPLGRTV  MLTVQFTLGW  PLYLAFNVSG  200
MJ02-313-1   KKSDIKWYGK  YLNNPLGRTV  MLTVQFTLGW  PLYLAFNVSG  200
MJ02-357-3   KKSDIKWYGK  YLNNPLGRTV  MLTVQFTLGW  PLYLAFNVSG  200

J96D-4830    RPYDGGFACH  FHPNAPIYND  RERLQIYISD  AGILAVCYGL  240
MJ02-086-3   RPYDGGFACH  FHPNAPIYND  RERLQIYISD  AGILAVCYGL  240
MJ02-313-1   RPYDGGFACH  FHPNAPIYND  RERLQIYISD  AGILAVCYGL  240
MJ02-357-3   RPYDGGFACH  FHPNALIYND  RERLQIYISD  AGILAVCYGL  240

J96D-4830    YRYAAVQGVA  SMVCFYGVPL  LIVNGFLVLI  TYLQHTHPSL  280
MJ02-086-3   YRYAAVQGVA  SMVCFYGVPL  LIVNGFLVLI  TYLQHTHPSL  280
MJ02-313-1   YRYAAVQGVA  SMVCFYGVPL  LIVNGFLVLI  TYLQHTHPSL  280
MJ02-357-3   YRYAAVQGVA  SMVCFYGVPL  LIVNGFLVLI  TYLQHTHPSL  280

J96D-4830    PHYDSSEWDW  LRGALATVDR  DYGILNKVFH  NITDTHVAHH  320
MJ02-086-3   PHYDSSEWDW  LRGALATVDR  DYGILNKVFH  NITDTHVAHH  320
MJ02-313-1   PHYDSSEWDW  LRGALATVDR  DYGILNKVFH  NITDTHVAHH  320
MJ02-357-3   PHYDSSEWDW  LRGALATVDR  DYGILNKVFH  NITDTHVAHH  320
```

FIGURE 5 CONTINUED

```
J96D-4830    LFSTMPHYHA MEATKAIKPI LGEYYQFDGT PVVKAMWREA  360
MJ02-086-3   LFSTMPHYHA MEATKAIKPI LGEYYQFDGT PVVKAMWREA  360
MJ02-313-1   LFSTMPHYHA MEATKAIKPI LGEYYQFDGT PVVKAMWREA  360
MJ02-357-3   LFSTMPHYHA MEATKAIKPI LGEYYQFDGT PVVKAMWREA  360

J96D-4830    KECIYVEPDR QGEKKGVFWY NNKL   384   SEQ ID NO:4
MJ02-086-3   KECIYVEPDR QGEKKGVFWY NNKL   384   SEQ ID NO:7
MJ02-313-1   KECIYVEPDR QGEKKGVFWY NNKL   384   SEQ ID NO:5
MJ02-357-3   KECIYVEPDR QGEKKGVFWY NNKL   384   SEQ ID NO:6
```

BRASSICA JUNCEA LINES WITH HIGH OLEIC ACID PROFILE IN SEED OIL

CROSS-REFERENCE TO RELATED APPLICATIONS

This application is a continuation-in-part of U.S. application Ser. No. 10/895,520, filed Jul. 20, 2004, now issued as U.S. Pat. No. 7,423,198, which is a continuation-in-part of U.S. application Ser. No. 10/330,775, filed Dec. 26, 2002, now issued as U.S. Pat. No. 7,605,301, which is hereby incorporated by reference in its entirety, and which claims priority to Canadian Application No. 2,382,767 filed on May 15, 2002. The present application also claims priority to Canadian Patent Application No. 2,619,858 filed on Feb. 22, 2008.

FIELD OF THE INVENTION

The invention is in the field of improved lines of *Brassica*, including *Brassica juncea*, improved oils from *Brassica juncea*, methods for generation of such lines, and methods for selection of such lines. More specifically certain embodiments relate to *Brassica* lines with an increased oleic acid content. All publications cited in this application are herein incorporated by reference.

BACKGROUND OF THE INVENTION

"Canola" generally refers to plants of *Brassica* species that have less than 2% erucic acid (Δ13-22:1) by weight in seed oil and less than 30 micromoles of glucosinolates per gram in meal. Typically, canola oil may contain less than about 7% total saturated fatty acids and greater than 60% oleic acid (as percentages of total fatty acids). Traditionally canola crops include *Brassica napus* and *Brassica rapa*. Recently, canola quality *Brassica juncea*, which has oil and meal qualities similar to other canola types, has been added to the canola crop family (U.S. Pat. No. 6,303,849, to Potts et al., issued on Oct. 16, 2001; U.S. Patent Publication No. 20030221217 of 27 Nov. 2003, Yao et al; Potts and Males, 1999; all of which are incorporated herein by reference).

Fatty acid compositions of vegetable oil affect the oil quality and stability. For example, oleic acid has been recognised to have health benefits including effectiveness in lowering plasma cholesterol levels and therefore, higher levels of oleic acid content in seed oil is a desirable trait. Further, not all fatty acids in vegetable oils are equally vulnerable to high temperature and oxidation. Rather, the susceptibility of individual fatty acids to oxidation is dependent on their degree of unsaturation. For example, linolenic acid, which has three carbon-carbon double bonds, is much more vulnerable to oxidation than oleic acid that has only one carbon-carbon double bond. High oleic acid content vegetable oil is also preferred because of its heat stability. For these reasons, high oleic acid and low linolenic acid may be desirable traits in plant oils.

Plants synthesize fatty acids in their plastid as palmitoyl-ACP (16:0-ACP) and stearoyl-ACP. The conversion of stearoyl-ACP to oleoyl-ACP (18:1-ACP) is catalyzed by a soluble enzyme, the stearoyl-ACP Δ9 desaturase (Shaklin and Somerville, 1991). These acyl-ACPs are either used for glycolipid synthesis in chloroplasts or transported out of chloroplasts into the cytoplasm as acyl-CoAs. Further desaturation of oleic acid occurs only after it is used in the synthesis of glycerolipids and incorporated into membranes, which leads to the synthesis of polyunsaturated fatty acids. The synthesis of polyunsaturated fatty acids linoleate (Δ9,12-18:2) and α-linolenate (Δ9,12,15-18:3) begins with the conversion of oleic acid (Δ9-18:1) to linoleic acid, the enzymatic step catalyzed by the microsomal ω-6 oleic acid desaturase (FAD2). The linoleic acid is then converted to α-linolenic acid through further desaturation by ω-3 linoleic acid desaturase (FAD3). There are reports that manipulation of the FAD2 gene through genetic engineering could alter fatty acid profiles. For example, heterologous expression of a soybean FAD2 gene in an *Arabidopsis* mutant line led to dramatic increase in the accumulation of polyunsaturated fatty acids (Heppard et al., 1996). In contrast, in an *Arabidopsis* mutant line fad2-5, where the transcription of the FAD2 gene was decreased significantly due to T-DNA insertion, showed a dramatic increase in the accumulation of oleic acid and a significant decrease in the levels of linoleic acid and linolenic acid (Okuley et al., 1994). These findings suggest that the FAD2 gene plays an important role in controlling conversion of oleic acid to linoleic acid in seed storage lipids.

Significant efforts have been made to manipulate the fatty acid profile of plants, particularly oil-seed varieties such as *Brassica* spp. that are used for the large-scale production of commercial fats and oils (see for example U.S. Pat. Nos. 5,625,130 issued 29 Apr. 1997; 5,668,299 issued 16 Sep. 1997; 5,767,338 issued 16 Jun. 1998; 5,840,946 issued 24 Nov. 1998; 5,850,026 issued 15 Dec. 1998; 5,861,187 issued 19 Jan. 1999; 6,063,947 issued 16 May 2000; 6,084,157 issued 4 Jul. 2000; 6,169,190 issued 2 Jan. 2001; 6,323,392 issued 27 Nov. 2001; and international patent applications WO 97/43907 published 27 Nov. 1997 and WO 00/51415 published 8 Sep. 2000).

*Brassica juncea* (AB genome) is an amphidiploid plant of the *Brassica* genus that is generally thought to have resulted from the hybridization of *Brassica rapa* (A genome) and *Brassica nigra* (B genome). *Brassica napus* (AC genome) is also an amphidiploid plant of the *Brassica* genera but is thought to have resulted from hybridization of *Brassica rapa* and *Brassica oleracea* (C genome). Under some growing conditions, *B. juncea* may have certain superior traits to *B. napus*. These superior traits may include higher yield, better drought and heat tolerance and better disease resistance. Intensive breeding efforts have produced plants of *Brassica* species whose seed oil contains less than 2% erucic acid and whose de-fatted meal contains less than 30 micro moles glucosinolates per gram. The term "canola" has been used to describe varieties of *Brassica* spp. containing low erucic acid (Δ13-22:1) and low glucosinolates. Typically, canola oil may contain less than about 7% total saturated fatty acids and greater than 60% oleic acid (as percentages of total fatty acids). For example, in the U.S., under 21 CFR 184.1555, low erucic acid rapeseed oil derived from *Brassica napus* or *Brassica* campestris is recognized as canola oil where it has an erucic acid content of no more than 2% of the component fatty acids (Table 1 sets out the Food Chemicals Codex (1996) specifications for canola oil). Plant breeders have also selected canola varieties that are low in glucosinolates, such as 3-butenyl, 4-pentenyl, 2-hydroxy-3-butenyl or 2-hydroxy-4-pentenyl glucosinolate. Canola quality meal may for example be defined as having a glucosinolate content of less than 30 micromoles of aliphatic glucosinolates per gram of oil-free meal. Currently, the principle commercial canola crops comprise *B. napus* and *B. rapa* (campestris) varieties. U.S. Pat. No. 6,303,849 issued to Potts et al. on 16 Oct. 2001 (incorporated herein by reference) discloses *B. juncea* lines having an edible oil that has properties similar to canola. The *B. juncea* lines disclosed therein have a lineage that includes *B. juncea* lines J90-3450 and J90-4316, deposited as ATCC Accession Nos 203389 and 203390 respectively (both of which were deposited by Agriculture and Agri-Food Canada under the terms of the Budapest Treaty on 23 Oct. 1998 at the American Type Culture Collection, University Blvd., Manassas, Va. USA 20110-2209).

TABLE 1

Food Chemicals Codex (1996) Specifications for Canola Oil

| Property Fatty Acids, % by weight | Canola Oil |
|---|---|
| <14 | <0.1 |
| 14:0 myristic | <0.2 |
| 16:0 palmitic | <6.0 |
| 16:1 | <1.0 |
| 18:0 | <2.5 |
| 18:1 oleic | >50.0 |
| 18:2 linoleic | <40.0 |
| 18:3 linolenic | <14.0 |
| 20:0 | <1.0 |
| 20:1 | <2.0 |
| 22:0 | <0.5 |
| 22:1 erucic | <2.0 |
| 24:0 | <0.2 |
| 24:1 | <0.2 |
| Acid value | <6 |
| Cold Test | Passes test |
| Colour(AOCS-Wesson) | ≦1.5R/15Y |
| Free fatty acids (as oleic) | <0.05% |
| Heavy metals (as Pb) | ≦5 mg/kg |
| Iodine value | 110-126 |
| Lead | <0.1 mg/kg |
| Peroxide value | ≦10 meq/kg |
| Refractive index | 1.465-1.467 |
| Saponifiable value | 178-193 |
| Stability | ≧7 h |
| Sulfur | ≦10 mg/kg |
| Unsaponifiable matter | ≦1.5% |
| Water | ≦0.1% |

The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with systems, tools and methods which are meant to be exemplary and illustrative, not limiting in scope. In various embodiments, one or more of the above described problems have been reduced or eliminated, while other embodiments are directed to other improvements.

Recently, high oleic acid (>70.0% by weight) *B. juncea* line, MJ02-086-3, bearing an ATCC Accession No. PTA-6907, has been disclosed (Yao et al., U.S. patent publication No. 20050039233, Feb. 17, 2005). Continued screening efforts have led to the discovery of two additional *B. juncea* lines, MJ02-3,3-1 and MJ02-357-3, also having >70.0% oleic acid in endogenous edible oil, which are disclosed in the current invention.

In various aspects, the invention provides *Brassica juncea* plants, seeds, cells, nucleic acid sequences and oils. Edible oil derived from plants of the invention may have significantly higher oleic acid content than other *B. juncea* plants. Three high oleic acid *Brassica juncea* lines are disclosed in the current invention. In one embodiment, the *B. juncea* line MJ02-313-1 contains a mutation at the BjFAD2-a gene locus and the resulting mutant allele MJ02-313-1/BjFAD2-a encodes a Glycine-94 Aspartic acid (G94A) mutation in the sequence of the predicted BjFAD2-a protein. In another embodiment, the *B. juncea* line MJ02-357-3 contains a different mutation at the BjFAD2-a gene locus and the resulting mutant allele MJ02-357-3/BjFAD2-a encodes a Proline-216 Leucine (P216L) mutation in the sequence of the predicted BjFAD2-a protein. In one embodiment, the *B. juncea* line MJ02-086-3 contains a mutation at the BjFAD2-a gene locus (premature translation stop caused by codon TGA in the BjFAD2-a gene) and the resulting mutant allele MJ02-086-3/BjFAD2-a encodes the premature translation stop mutation in the sequence of the predicted BjFAD2-a protein. Seeds from MJ02-313-1, MJ02-357-3 and MJ02-86-3 mutant lines may for example yield an oil having oleic acid content of greater than 70.0% by weight.

In one aspect of the invention, it has unexpectedly been discovered that the deletion or silencing of all activity of FAD2 enzymes in a *Brassica* plant yields plants capable of producing an oil having oleic acid content of greater than about 70% by weight. Such plants may for example be tetraploid plants or amphidiploid plants, such as *Brassica juncea*, or *Brassica napus*. In one aspect, the invention accordingly provides for the deletion or silencing of selected FAD2 coding sequences in a plant, such as in lines of *B. juncea* or *B. napus*. Edible oil derived from plants of the invention may be characterised by one or more of the following characteristics: an oleic acid content of at least 70% by weight, a linoleic acid content of less than 10% by weight, a linolenic acid content of less than 10% by weight, an erucic acid content of less than 1% by weight, and a total saturated fatty acid content of less than 7.1% by weight. In some embodiments, the invention provides low erucic acid oil derived from tetraploid plants having no expressible FAD2 coding sequences, such as *B. juncea* plants, that will meet one or more of the specifications for low erucic acid rapeseed oil in the Food Chemicals Codex, 4th edition (1996), as set out in Table 1.

Alternative aspects of the invention include plants and plant parts. As used herein, "plant parts" includes plant cells, seeds, pollen bearing the nucleic acids of the invention or having the FAD2 coding sequences of the invention or having regulatory sequences, such as sequences upstream of FAD2 coding regions, that inhibit expression of all FAD2 coding sequences. Methods are provided for using the plants of the invention, including progeny plants selected by markers of the invention, to obtain plant products. As used herein, "plant products" includes anything derived from a plant of the invention, including plant parts such as seeds, meals, fats or oils, including plant products having altered oleic acid concentrations. Methods are provided for modifying plants so that they have no FAD2 coding sequences capable of expressing an active FAD2 enzyme. Such methods may for example involve inactivating one or more of the FAD2 coding sequences in a plant, so that the plant has no expressible FAD2 coding sequences.

Amplification primers for identifying portions of the FAD2 coding sequences of the invention are provided, which may be used for example to distinguish different alleles of a selected FAD2 locus. Methods are provided for obtaining plants using the FAD2 coding sequences of the invention, or regions upstream of the FAD2 coding sequences of the invention. For example, sequences of the invention may be used to guide or target site-specific mutations that may down-regulate expression of selected FAD2 coding sequences, such as by down-regulating the expression of a FAD2 gene from a selected FAD2 locus or by truncating the FAD2 protein encoded by the FAD2 gene. Conventional plant breeding techniques such as crossing and backcrossing and other breeding techniques may be used to introduce the FAD2 coding sequences of the invention into progeny of the plants of the invention.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 2 shows the nucleotide sequence of the BjFAD2-a gene of the line J96D-4830 (SEQ ID NO:1). The putative upstream non-coding region is shown in lower case and the open reading frame (ORF) is shown in upper case. The potential TATA box of the gene is shown in bold and underlined.

FIG. 3 shows the nucleotide sequence of the BjFAD2-a gene of the line MJ02-313-1 (SEQ ID NO:2). The putative upstream non-coding region is shown in lower case and ORF is shown in upper case. The potential TATA box is shown in bold and underlined. The mutation codon GAC in the ORF, which causes the Glycine-94 Aspartic acid mutation, is shown in bold and underlined.

FIG. 4 shows the nucleotide sequence of the BjFAD2-a gene of the mutant line MJ02-357-3 (SEQ ID NO:3). The putative upstream non-coding region is shown in lower case and ORF is shown in upper case. The potential TATA box is shown in bold and underlined. The mutation codon CTC in the ORF, which causes the Proline-216 Leucine mutation, is shown in bold and underlined.

FIG. 5 shows the alignment of predicted BjFAD2-a amino acid sequences including wild-type line J96D-4830 (SEQ ID NO:4), mutant line MJ02-313-1 (SEQ ID NO:5), mutant line MJ02-357-3 (SEQ ID NO:6) and mutant line MJ02-086-3 (SEQ ID NO:7). The mutations in MJ02-313-1 (G94D) and MJ02-357-3 (P216L) are shown in bold and underlined. The predicted BjFAD2-a sequences from wild type line J96D-4830 and mutant line MJ02-086-3 are included for reference. The symbol * denotes the premature translation stop caused by codon TGA in the BjFAD2-a gene of line MJ02-086-3.

DETAILED DESCRIPTION OF THE INVENTION

Figure 1:
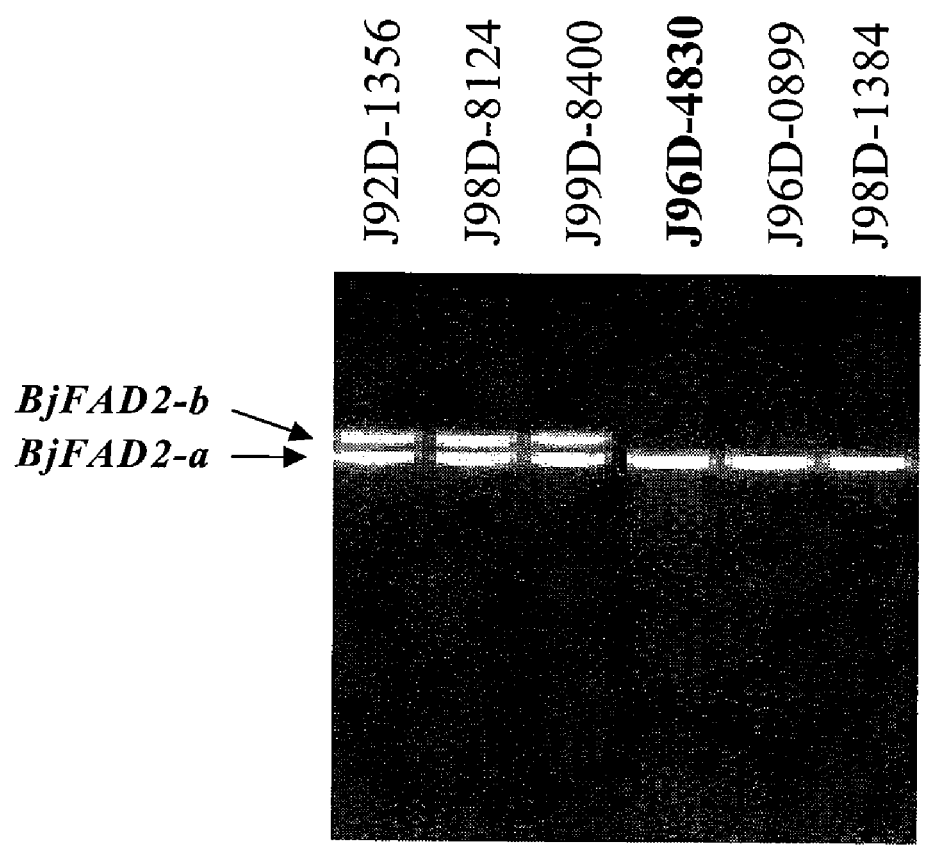
FIG. 1 shows the image of an Agarose gel illustrating the results of PCR amplifications using leaf genomic DNA of FAD2 gene loci, BjFAD2-b and BjFAD2-a, from various Brassica juncea lines. Three lines are original low erucic acid/low oleic acid Brassica juncea (J92D-1356, J96D-3124, J99D-8400). The other three lines are canola quality Brassica juncea (J96D-4830, J96D-0899, J98D-1384). PCR amplifications were performed using primers FAD2Pup-1 and FAD2low. Migration positions of the BjFAD2-b and BjFAD2-a genes on the agarose gel after electrophoresis are marked.

For clarity of description, some of the terminology used herein is explained as follows.

The term "line" refers to a group of plants that displays very little overall variation among individuals sharing that designation. A "line" generally refers to a group of plants that display little or no genetic variation between individuals for at least one trait. A "DH (doubled haploid) line", as used in this application refers to a group of plants generated by culturing a haploid tissue and then doubling the chromosome content without accompanying cell division, to yield a plant with the diploid number of chromosomes where each chromosome pair is comprised of two duplicated chromosomes. Therefore, a DH line normally displays little or no genetic variation between individuals for traits.

A "variety" or "cultivar" is a line that is used for commercial production. A "doubled haploid" (DH) line refers to a line created by the process of microspore embryogenesis, in which a plant is created from an individual microspore. By this process, lines are created that are homogeneous, i.e. all plants within the line have the same genetic makeup. The original DH plant is referred to as DH1, while subsequent generations are referred to as DH2, DH3 etc. Doubled haploid procedures are well known and have been established for several crops. A procedure for B. juncea has been described by Thiagrarajah and Stringham (1993) (A comparison of genetic segregation in traditional and microspore-derived populations of Brassica juncea in: L. Czern and Coss. Plant Breeding 111:330-334).

The term "high oleic" refers to B. juncea or other Brassica species as the context may dictate, with an oleic acid content higher than that of a wild type or other reference variety or line, most generally it indicates a fatty acid composition comprising at least 70.0% by weight oleic acid.

"Total saturates" refers to the combined percentages of palmitic (C-16:0), stearic (C-18:0), arachidic (C-20:0), behenic (C-22:0) and tetracosanoic (24:0) fatty acids. The fatty acid concentrations discussed herein are determined in accordance with standard procedures well known to those skilled in the art. Specific procedures are elucidated in the examples. Fatty acid concentrations are expressed as a percentage by weight of the total fatty acid content.

"Halfseed" analysis refers to a procedure whereby fatty acid analysis is carried out on one cotyledon (halfseed) and the remaining halfseed is used to form a plant if the results of the analysis are positive.

"Mutagenesis" is a process in which an agent known to cause mutations in genetic material is applied to plant material. In the experimental work, the mutagenic agent used was ethyl methylsulfonate (EMS). The purpose is to cause new genetic variability in a species and is usually done with a specific trait in mind. An example of mutagenesis used on haploids to induce novel variation has been described by Swanson et al. (Plant Cell Rep. 7:83-87, 1988). The disclosure of this article is herein incorporated by reference. It will be appreciated that a range of other techniques such as recombination with foreign nucleic acid fragments may be suitable to generate mutants and that by using certain techniques the generation of mutants may be directed at specific nucleotide or amino acid changes rather than being entirely random. All such methods of introducing nucleic acid sequence changes are understood to be included within the term "mutagenesis" as used herein.

"Regeneration" involves the selection of cells capable of regeneration (e.g. seeds, microspores, ovules, pollen, vegetative parts) from a selected plant or variety. These cells may optionally be subjected to mutagenesis, following which a plant is developed from the cells using regeneration, fertilization, and/or growing techniques based on the types of cells mutagenized. Applicable regeneration techniques are known to those skilled in the art; see, for example, Armstrong, C. L., and Green, C. E., Planta 165:322-332 (1985); and Close, K. R., and Ludeman, L. A., Planta Science 52:81-89 (1987), the disclosures of which are incorporated herein by reference. In this context, "$M_0$" refers to untreated seeds; "$M_1$" refers to the seeds exposed to mutagens and the resulting plants; "$M_2$" is the progeny (seeds and plants) of self-pollinated $M_1$ plants; "$M_3$" is the progeny (seeds and plants) of self-pollinated $M_2$ plants; "M₄" is the progeny (seeds and plants) of self-pollinated M₃ plants; "M₅" is the progeny (seeds and plants) of self-pollinated M₄ plants, and so on.

In this application sequences disclosed may be used to prepare antibodies to the associated proteins, using standard techniques of preparation as, for example, described in Harlow and Lane (Harlow and Lane Antibodies; A Laboratory Manual, Cold Spring Harbor Laboratory, Cold Spring Harbor, N.Y., 1988), or known to those skilled in the art.

For example, a coding sequence for a polypeptide of the invention may be purified to the degree necessary for immunization of rabbits. To attempt to minimize the potential problems of low affinity or specificity of antiserum, two or three polypeptide constructs may be generated for each protein, and each construct is injected into at least two rabbits. Antisera may be raised by injections in a series, preferably including at least three booster injections. Primary immunizations may be carried out with Freund's complete adjuvant and subsequent immunizations with Freund's incomplete adjuvant. Antibody titers may be monitored by Western blot and immunoprecipitation analyses using the purified protein. Immune sera may be affinity purified using CNBr-Sepharose-coupled protein. Antiserum specificity may be determined using a panel of unrelated proteins.

Alternatively or additionally, peptides corresponding to relatively unique immunogenic regions of a polypeptide of the invention may be generated and coupled to keyhole limpet hemocyanin (KLH) through an introduced C-terminal lysine. Antiserum to each of these peptides may be affinity purified on peptides conjugated to BSA, and specificity tested in ELISA and Western blots using peptide conjugates and by Western blot and immunoprecipitation.

Alternatively, monoclonal antibodies which specifically bind any one of the polypeptides of the invention are prepared according to standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981). Once produced, monoclonal antibodies may also be tested for specific recognition by Western blot or immunoprecipitation. Antibodies which specifically bind the polypeptide of the invention are considered to be useful; such antibodies may be used, e.g., in an immunoassay. Alternatively monoclonal antibodies may be prepared using the polypeptide of the invention described above and a phage display library (Vaughan et al., Nature Biotech 14:309-314, 1996).

In some embodiments, antibodies may be produced using polypeptide fragments that appear likely to be immunogenic, by criteria such as high frequency of charged residues. Antibodies can be tailored to minimise adverse host immune response by, for example, using chimeric antibodies contain an antigen binding domain from one species and the Fc portion from another species, or by using antibodies made from hybridomas of the appropriate species.

In some embodiments, antibodies against any of the polypeptides described herein or inferrable herefrom may be employed to determine the presence or expression of one of the alleles disclosed and to distinguish between mutated and wild type proteins or other mutants.

In this application "improved characteristics" means that the characteristics in question are altered in a way that is desirable or beneficial or both in comparison with a reference value or attribute, which may relate to the equivalent characteristic of a wild type strain of *Brassica juncea*, or of whichever other *Brassica* line is under consideration. One possible wild type *Brassica juncea* strain whose characteristics may be taken as a reference (or a control) is J96D-4830 but many others are possible and will readily be identified by those skilled in the art.

In this application "progeny" means all descendants including offspring and derivatives of a plant or plants and includes the first, second, third and subsequent generations and may be produced by self-pollination or crossing with plants with the same or different genotypes, and may be modified by a range of suitable genetic engineering techniques.

In this application "breeding" includes all methods of developing or propagating plants and includes both intra- and inter-species and intra- and inter-line crosses as well as all suitable conventional breeding and artificial breeding techniques. Desired traits may be transferred to other *Brassica juncea* lines through conventional breeding methods and can also be transferred to other *Brassica* species, such as *Brassica napus* and *Brassica rapa* through inter-specific crossing. Both conventional breeding methods and inter-specific crossing methods as well as other methods of transferring genetic material between plants are well documented in the literature.

In this application "molecular biological techniques" means all forms of manipulation of a nucleic acid sequence to alter the sequence and expression thereof and includes the insertion, deletion or modification of sequences or sequence fragments and the direct introduction of new sequences into the genome of an organism by directed or random recombination using any suitable vectors and/or techniques.

In this application "genetically derived" as used for example in the phrase "genetically derived from the parent lines" means that the characteristic in question is dictated wholly or in part by an aspect of the genetic makeup of the plant in question.

In this application the term "*Brassica*" may comprise any or all of the species subsumed in the genus *Brassica* including *Brassica napus, Brassica juncea*, and *Brassica rapa*.

Canola *Brassica juncea* as used in this application refers to *Brassica juncea* that produces seeds with oil and meal quality that meets the requirements for a commercial designation as canola oil or meal, respectively.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

All percentages of fatty acids herein refer to percentage by weight of total fatty acids of oil in which the fatty acid is a component. For example, reference to a plant having a 70% oleic acid content indicates that the fatty acid component of the oil comprises 70% oleic acid.

"Polymorphism" in a population refers to a condition in which the most frequent variant (or allele) of a particular locus has a population frequency which does not exceed 99%.

The term "heterozygosity" (H) is used when a fraction of individuals in a population have different alleles at a particular locus (as opposed to two copies of the same allele). Heterozygosity is the probability that an individual in the population is heterozygous at the locus. Heterozygosity is usually expressed as a percentage (%), ranging from 0 to 100%, or on a scale from 0 to 1.

"Homozygosity" or "homozygous" indicates that a fraction of individuals in a population have two copies of the same allele at a particular locus. Where plants are double haploid it is presumed that subject to any spontaneous mutations occurring during duplication of the haplotype, all loci are homozygous. Plants may be homozygous for one, several or all loci as the context indicates.

"Primers" are short polynucleotides or oligonucleotides required for a polymerase chain reaction that are complementary to a portion of the polynucleotide to be amplified. For example, the primer may be no more than 50 nucleotides long, preferably less than about 30 nucleotides long, and most preferably less than about 24 nucleotides long.

An "isolated" nucleic acid or polynucleotide as used herein refers to a component that is removed from its original environment (for example, its natural environment if it is naturally occurring). An isolated nucleic acid or polypeptide may contain less than 50%, less than 75%, less than 90%, and less than 99.9% or less than any integer value between 50 and 99.9% of the cellular components with which it was originally associated. A polynucleotide amplified using PCR so that it is sufficiently distinguishable (on a gel from example) from the rest of the cellular components may for example, be considered "isolated". The polynucleotides of the invention may be "substantially pure", i.e., having the highest degree of purity that can be achieved using a particular purification technique known in the art.

"Hybridization" refers to a process in which a strand of nucleic acid joins with a complementary strand through base pairing. Polynucleotides are "hybridisable" to each other when at least one strand of one polynucleotide can anneal to a strand of another polynucleotide under defined stringency conditions. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences. (1×SSC is 0.15 M NaCl, 0.015 M Na citrate.) As used herein, the above solutions and temperatures refer to the probe-washing stage of the hybridization procedure. The term "a polynucleotide that hybridizes under stringent (low, intermediate) conditions" is intended to encompass both single and double-stranded polynucleotides although only one strand will hybridize to the complementary strand of another polynucleotide. Washing in the specified solutions may be conducted for a range of times from several minutes to several days and those skilled in the art will readily select appropriate wash times to discriminate between different levels of homology in bound sequences.

In one aspect, the invention provides *Brassica* plants, such as *Brassica juncea* plants, capable of producing seeds having an endogenous fatty acid content comprising a high percentage of oleic acid by weight. Seeds of the invention may also have a low percentage of erucic acid and linoleic acid by weight. In particular embodiments, the oleic acid may comprise more than about 70.0%, 71.3%, 72.9%, 73.3%, 74.5%, 75.3%, 76.6%, 77.8%, 78.4%, 79.5% 80.0%, 81.5%, 82.6%, 83.4%, 84.8% or 85.0% and including all integers and fractions thereof or any integer value greater than 85% of the fatty acids. In particular embodiments the erucic acid content of the fatty acids may be less than about 1%, 0.9%, 0.8%, 0.7%, 0.6%, or 0.5% or 0% and including all integers and fraction thereof. In particular embodiments the linoleic acid content may be less than about 10.0%, 9.2%, 8.6%, 7.1%, 6.5%, 5.2%, 4.3%, 3.0%, 2.4% or 1.5% and including all integers and fractions thereof. In one exemplary embodiment, the plant is *Brassica juncea*, whose seeds have an endogenous fatty acid content comprising at least 70% oleic acid by weight, and less than 1% erucic acid by weight. In an additional embodiment, the plant is a *Brassica juncea* plant whose seeds have an endogenous fatty acid content comprising 70.0%, 71.3%, 72.5%, 73.9%, 74.0%, 75.3%, 76.5%, 77.9%, 78.0%, 79.3%, 80.5%, 81.7%, 82.9%, 83.5% or 84.0% and all including all integers and fractions thereof, oleic acid by weight, and no more than 1% erucic acid by weight.

In selected embodiments, plants of the current invention may be *Brassica juncea* plants of line MJ02-313-1 (ATCC Accession No. PTA-7955) or may be progeny plants of line MJ02-313-1. In alternative selected embodiments, plants of the current invention may be *Brassica juncea* plants of line MJ02-357-3 (ATCC Accession No. PTA-7956) or may be progeny plants of line MJ02-357-3.

In an alternative aspect, the invention provides methods for increasing the oleic acid content of *Brassica* plants. Such methods may involve: (a) inducing mutagenesis in at least some cells from a *Brassica* line that has an oleic acid content >55%; (b) regenerating plants from at least one of said mutagenized cells and selecting regenerated plants which have a fatty acid content comprising at least 70% oleic acid (or an alternative threshold concentration of oleic acid, as set out above); and (c) deriving further generations of plants from said regenerated plants, individual plants of said further generations of plants having a fatty acid content comprising at least 70% oleic acid (or the alternative threshold concentration). In some embodiments the *Brassica* may be *Brassica juncea*. The term "high oleic acid content" encompasses the full range of possible values described above. In alternative embodiments, methods of the invention may further comprise selecting one or more of the lines, the regenerated plants and the further generations of plants for reduced linoleic acid content, such as the range of possible values described above. In further embodiments step (c) may involve selecting and growing seeds from the regenerated plants of step (b). In further embodiments, methods of the invention may comprise repetition of the specified steps until the desired oleic acid content, linoleic acid content, or both, are achieved.

In alternative embodiments, methods are provided for screening individual seeds for increased oleic acid content, and/or decreased linoleic acid content, comprising: determining one or more of the oleic acid content; or the linoleic acid content; or the oleic acid content and the linoleic acid content of the fatty acids of a part of the germinant of the seed; comparing one or more of the contents with a reference value; and inferring the likely relative oleic acid, linoleic acid, or oleic and linoleic acid content of the seed. In particular embodiments the part of the plant used for analysis may be part or all of a leaf, cotyledon, stem, petiole, stalk or any other tissue or fragment of tissue, such as tissues having a composition that demonstrates a reliable correlation with the composition of the seed. In one series of embodiments the part of the germinant may be a part of a leaf. In certain embodiments the step of inferring the fatty acid composition of the seed may comprise assuming that a significantly changed level of a given acid in said leaf reflects a similar relative change in the level of that acid in the seed. In a particular embodiment of this invention, a method for screening Brassica plants for individual plant line whose seeds have an endogenous fatty acid content comprising at least 70% oleic acid by weight by analyzing leaf tissue. In addition, the leaf tissue can be analyzed for fatty acid composition by gas liquid chromatography, wherein the extraction of the fatty acids can occur by methods such as bulk-seed analysis or half-seed analysis.

In alternative embodiments the invention provides Brassica plants, which may be Brassica juncea plants, comprising the MJ02-313-1/BjFAD2-a allele at the BjFAD2-a locus. The allele, MJ02-313-1/BjFAD2-a, means the gene allele from the B. juncea line MJ02-313-1. In certain embodiments the plant may be homozygous at the BjFAD2-a locus represented by the mutant MJ02-313-1/BjFAD2-a allele. In an additional embodiment, the B. juncea plant, plant cell, or a part thereof, contains the MJ02-313-1/BjFAD2-a allele having nucleic acid sequence SEQ ID NO:2. In alternative embodiments the invention provides Brassica plants, which may be Brassica juncea plants, comprising the MJ02-357-3/BjFAD2-a allele at the BjFAD2-a locus. The allele, MJ02-357-3/BjFAD2-a, means the gene allele from the B. juncea line MJ02-357-3. In certain embodiments the plant may be homozygous at the BjFAD2-a locus represented by the mutant MJ02-357-3/BjFAD2-a allele. In an additional embodiment, the B. juncea plant, plant cell, or a part thereof, contains the MJ02-357-3/BjFAD2-a allele having nucleic acid sequence SEQ ID NO:3.

In some embodiments, the invention may involve distinguishing canola quality Brassica juncea (~60% oleic acid) from the low erucic/low oleic acid Brassica juncea (~45% oleic acid) by examining the presence or absence of the BjFAD2-b gene (see for reference U.S. patent publication No. 20030221217, Yao et al.). This distinction may involve confirming that the BjFAD2-a gene is the only functional oleate fatty acid desaturase gene in a canola quality Brassica juncea line, such as J96D-4830 (See FIG. 1 for the determination of the presence or absence of the BjFAD2-b gene). In alternative embodiments, the invention provides plants, such as plants of the line MJ02-313-1, having a mutation at the BjFAD2-a gene locus (see FIG. 3 for nucleotide sequence; SEQ ID No:2). Aspects of the invention therefore involve the recognition that the MJ02-313-1/BjFAD2-a allele is a mutant allele compared to the J96D-4830/BjFAD2-a wild type allele (see FIG. 2 for J96D-4830/BjFAD2-a nucleotide sequence; SEQ ID No:1). In other embodiments, the invention provides plants, such as plants of the line MJ02-357-3, having a different mutation at the BjFAD2-a gene locus (see FIG. 4 for nucleotide sequence; SEQ ID No:3). Aspects of the invention therefore involve the recognition that the MJ02-357-3/BjFAD2-a allele is a mutant allele compared to the J96D-4830/BjFAD2-a wild type allele (see FIG. 2 for J96D-4830/BjFAD2-a nucleotide sequence; SEQ ID No:1).

In alternative embodiments, the invention provides nucleic acids, such as isolated or recombinant nucleic acid molecules, comprising the sequence of the MJ02-313-1/BjFAD2-a allele (SEQ ID No: 2) and the sequences of the MJ02-357-3/BjFAD2-a allele (SEQ ID No: 3) of the invention. The invention provides for an isolated nucleic acid molecule comprising a nucleotide sequence encoding a polypeptide having SEQ ID NO:5 or having SEQ ID NO:6. The invention also provides an isolated nucleic acid molecule comprising a sequence having at least 95% sequence identity to SEQ ID NO:2 or having at least 95% sequence identity to SEQ ID NO:3. Isolated nucleic acids of the invention may include coding sequences of the invention recombined with other sequences, such as cloning vector sequences. The invention also provides for a vector comprising the isolated nucleic acid molecule comprising a sequence having at least 95% sequence identity to SEQ ID NO:2 or a vector comprising the isolated nucleic acid molecule comprising a sequence having at least 95% sequence identity to SEQ ID NO:3. Homology to sequences of the invention may be detectable by hybridization with appropriate nucleic acid probes, by PCR techniques with suitable primers or by any other commonly used techniques. In particular embodiments there are provided nucleic acid probes which may comprise sequences homologous to portions of the alleles of the invention. Further embodiments may involve the use of suitable primer pairs to amplify or detect the presence of a sequence of the invention, for example a sequence that is associated with increased oleic acid content.

The following terms are used to describe the sequence relationships between two or more nucleic acids or polynucleotides: (a) "reference sequence", (b) "comparison window", (c) "sequence identity", (d) "percentage of sequence identity", and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS 4:11-17; the local homology algorithm of Smith et al. (1981) Adv. Appl. Math. 2:482; the homology alignment algorithm of Needleman and Wunsch (1970) J. Mol. Biol. 48:443-453; the search-for-similarity-method of Pearson and Lipman (1988) Proc. Natl. Acad. Sci. 85:2444-2448; the algorithm of Karlin and Altschul (1990) Proc. Natl. Acad. Sci. USA 872264, modified as in Karlin and Altschul (1993) Proc. Natl. Acad. Sci. USA 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) J. Mol. Biol. 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

In selected embodiments, the invention provides isolated DNA sequences comprising complete open reading frames (ORFs) and/or 5' upstream regions of the BjFAD2-a gene, for example from the mutant lines MJ02-313-1 and MJ02-357-3. For comparison, homologous sequences are disclosed from the wild type line J96D-4830. Specifically, the mutant allele, MJ02-313-1/BjFAD2-a (SEQ ID NO:2), has a single basepair change (a G to A transition) compared to the corresponding wild type allele J96D-4830/BjFAD2-a (SEQ ID NO:1), which occurs in the ORF of the BjFAD2-a gene. This single basepair mutation changes the codon GGC (encoding Gly) of the wild type J96D-4830/BjFAD2-a allele to the codon GAC (encoding Asp) in the mutant MJ02-313-1/BjFAD2-a allele. The mutant allele, MJ02-357-3/BjFAD2-a (SEQ ID NO:3), has a different single basepair change (a C to T transition) compared to the corresponding wild type allele J96D-4830/BjFAD2-a, which also occurs in the ORF of the BjFAD2-a gene. As a result, this single basepair mutation changes the codon CCC (encoding Pro) of the wild type J96D-4830/BjFAD2-a allele to the codon CTC (encoding Leu) in the mutant MJ02-357-3/BjFAD2-a allele. The invention accordingly provides a polypeptide sequence of the predicted mutant protein, containing a Glycine-94 Aspartic acid (G94A) mutation from the mutant MJ02-313-1/BjFAD2-a allele. The invention accordingly also provides a polypeptide sequence of the predicted mutant protein, containing a proline-216 Leucine (P216L) mutation from the mutant MJ02-357-3/BjFAD2-a allele. It is known that membrane-bound desaturases, such as FAD2, have conserved histidine boxes. Changes in amino acid residues outside these histidine boxes may also affect the FAD2 enzyme activity (Tanhuanpää et al., Molecular Breeding 4: 543-550, 1998).

In one aspect of the invention, the mutant alleles MJ02-313-1/BjFAD2-a and MJ02-357-3/BjFAD2-a may be used in plant breeding. Specifically, alleles of the invention may be used for breeding high oleic acid *Brassica* species, such as *B. juncea, B. napus, B. rapa, B. nigra* and *B. carinata*. The invention provides molecular markers for distinguishing mutant alleles, such as the MJ02-313-1/BjFAD2-a allele and MJ02-357-3/BjFAD2-a allele, from alternative sequences, such as the wild type J96D-4830/BjFAD2-a allele. The invention thereby provides methods for segregation and selection analysis of genetic crosses involving plants having alleles of the invention, such as the MJ02-313-1/BjFAD2-a allele and MJ02-357-3/BjFAD2-a allele. The invention thereby provides methods for segregation and selection analysis of progenies derived from genetic crosses involving plants having alleles of the invention, such as the MJ02-313-1/BjFAD2-a allele and MJ02-357-3/BjFAD2-a allele.

In alternative embodiments, the invention provides methods for identifying *Brassica* plants, such as *Brassica juncea* plants, with a desirable fatty acid composition or a desired genomic characteristic. Methods of the invention may for example involve determining the presence in a genome of particular FAD2 alleles, such as the MJ02-313-1/BjFAD2-a allele, MJ02-357-3/BjFAD2-a, or the wild type J96D-4830/BjFAD2-a allele. In particular embodiments the methods may comprise identifying the presence of a nucleic acid polymorphism associated with one of the identified alleles or an antigenic determinant associated with one of the alleles. Such a determination may for example be achieved with a range of techniques, such as PCR amplification of the relevant DNA fragment, DNA fingerprinting, RNA fingerprinting, gel blotting and RFLP analysis, nuclease protection assays, sequencing of the relevant nucleic acid fragment, the generation of antibodies (monoclonal or polyclonal), or alternative methods adapted to distinguish the protein produced by the relevant alleles from other variants or wild type forms of that protein. This invention also provides a method for identifying *B. juncea* plants, whose seeds have an endogenous fatty acid content comprising at least 70% oleic acid by weight, by determining the presence of the mutant MJ02-313-1/BjFAD2-a allele or the mutant MJ02-357-3/BjFAD2-a allele.

In one of the selected embodiments, the specific single basepair change of the MJ02-313-1/BjFAD2-a mutant allele may be used to design an allele-specific PCR primer, for example making use of a 3' mismatch. Various primer combinations can be made, such as forward primers or reverse primers with a "G/C" at the 3' end (for amplifying that wild type allele) or an "A/T" at the 3' end (for amplifying the mutant allele). In another selected embodiments, the specific single basepair change of the MJ02-357-3/BjFAD2-a mutant allele may be used to design an allele-specific PCR primer, for example making use of a 3' mismatch. Various primer combinations can be made, such as forward primers or reverse primers with a "C/G" at the 3' end (for amplifying that wild type allele) or a "T/A" at the 3' end (for amplifying the mutant allele). For an exemplary summary of allele-specific PCR protocols, see Myakishev et al., 2001, Genome Research 11: 163-169, or Tanhuanpaa et al., 1999, Molecular Breeding 4: 543-550.

In alternative embodiments, various methods for detecting single nucleotide polymorphisms (SNPs) may be used for identifying alleles of the invention, such as the MJ02-313-1/BjFAD2-a allele (SEQ ID NO:2) or MJ02-357-3/BjFAD2-a allele (SEQ ID NO:3). Such methods may for example include TaqMan assays or Molecular Beacon assays (Tapp et al., BioTechniques 28: 732-738), Invader Assays (Mein et al., Genome Research 10: 330-343, 2000) or assays based on single strand conformational polymorphisms (SSCP) (Orita et al., Proc. Natl. Acad. Sci. U.S.A. 86: 2766-2770, 1989).

In alternative embodiments, the invention provides *Brassica* plants comprising FAD2 coding sequences that encode mutated FAD2 proteins, such as the MJ02-313-1/BjFAD2-a allele or MJ02-357-3/BjFAD2-a allele or a portion thereof of each allele. Such mutated FAD2 proteins may contain only one amino acid change compared to the wild type FAD2 protein. In one selected embodiment, the *Brassica juncea* line MJ02-313-1 contains a mutated FAD2 protein (SEQ ID NO:5), defined as Glycine-94 Aspartic acid (G94A) mutation, encoded by the MJ02-313-1/BjFAD2-a allele (SEQ ID NO:2). In another selected embodiment, the *Brassica juncea* line MJ02-357-3 contains a mutated FAD2 protein (SEQ ID NO:6), defined as Proline-216 Leucine (P216L) mutation, encoded by the MJ02-357-3/BjFAD2-a allele (SEQ ID NO:3). Such alleles may be selected to be effective to confer an increased oleic acid content on plants of the invention. In particular embodiments, the desired allele may be introduced into plants by breeding techniques. In alternative embodiments, alleles of the invention may be introduced by molecular biological techniques, including plant transformation. In such embodiments, the plants of the invention may produce seed having an endogenous fatty acid content comprising: at least about 70% oleic acid by weight, or any other oleic acid content threshold as set out above. Plants of the invention may also contain 1.5% to 10% by weight linoleic acid, from 5.0% to 10% by weight linolenic acid, from 0% to 1% erucic acid, 1.0% to 2.5% stearic acid, and have a total fatty acid content of from less than 7.1% to less than about 6.2% by weight, wherein the oil composition is genetically derived from the parent line. In one embodiment, the plant produces seed having an endogenous fatty acid content comprising at least about 70% of oleic acid, less than 10% of linoleic acid, less than, less than 10% of linolenic acid, less than 1% of erucic acid, and less than 2.5% stearic acid, wherein the oil composition is genetically derived from the parent line.

In selected embodiments, the invention provides *Brassica* seed, which may be a *Brassica juncea* seed, having an endogenous oil content having the fatty acid composition set out for one or more of the foregoing embodiments and wherein the genetic determinants for endogenous oil content are derived from either line MJ02-313-1 or MJ02-357-3. Such seeds may for example be obtained by selfing the line MJ02-313-1 (ATCC Accession Number PTA-7955) or by selfing the line MJ02-357-3 (ATCC Accession Number PTA-7956). Alternatively, such seeds may for example be obtained by crossing MJ02-313-1 or MJ02-357-3 with a second parent followed by selection, wherein the second parent can be any other *Brassica* lines such as a *B. juncea* line, being a canola quality *B. juncea* or a non-canola quality *B. juncea*, or any other *Brassica* species such as *B. napus, B. rapa, B. nigra*, and *B. carinata*. These breeding techniques are well known in the art.

In alternative embodiments the invention provides genetically stable plants of the genus *Brassica*, such as *Brassica juncea* plants, that develop mature seeds having a composition disclosed in one or more of the foregoing embodiments. Such plants may for example be derived from *B. juncea* lines MJ02-313-1 or MJ02-357-3. The oil composition of such plants may be genetically derived from the parent lines.

In alternative embodiments the invention provides processes of producing a genetically stable *Brassica* plant, such as a *B. juncea* plant, that produces mature seeds having an endogenous fatty acid content comprising the composition specified for one or more of the foregoing embodiments. Processes of the invention may involve the steps of: crossing B. juncea line MJ02-313-1 with other Brassica plants or crossing B. juncea line MJ02-357-3 with other plants, as described above, to form F1 progenies. The F1 progenies may be propagated, for example by means that may include self-pollination or the development of doubled haploid plants. The resulting progenies may be subject to selection for genetically stable plants that generate seeds having a composition disclosed for one or more of the foregoing embodiments. Such seeds may for example have a stabilized fatty acid profile that includes a total saturates content of from about 7.1% to about 6.5% in total extractable oils. The stabilized fatty acid profile may be derived from B. juncea line MJ02-313-1, for example by inheritance of the allele MJ02-313-1/BjFAD2-a. Alternatively, the stabilized fatty acid profile may be derived from B. juncea line MJ02-357-3, for example by inheritance of the allele MJ02-357-3/BjFAD2-a. In certain variants the progeny may themselves produce seeds or oil that has a composition as set out above for alternative embodiments.

In selected embodiments, an increase in oleic acid in plants of the invention, such as plants derived from line MJ02-313-1 or from line MJ02-357-3, may be accompanied by a corresponding decrease in linoleic acid and linolenic acid, while other fatty acids may remain virtually unchanged. For example, the linoleic acid decreases from about 16.72% to about 1.81% in line MJ02-313-1 and to about 3.96% in line MJ02-357-3. The linolenic acid decreases from 11.97% to 5.24% in line MJ02-313-1 and 9.34% in line MJ02-357-3 (see Table 3 for detailed changes in fatty acid profile).

In some embodiments, the mutant FAD2 alleles of the invention (e.g. MJ02-313-1/BjFAD2-a allele or MJ02-357-3/BjFAD2-a allele) may be combined with additional mutant alleles in fatty acid enzymes, such as mutant FAD3 alleles. For example, the MJ02-313-I line may be used to provide FAD2 mutant in crosses with another Brassica parent plant (such as B. juncea, B. rapa, B. napus, B. nigra and B. carinata) with a FAD3 gene mutation. In the same way, the MJ02-357-3 line may be used to provide FAD2 mutant in crosses with another parent plant with a FAD3 gene mutation. The plants created in such ways contain double mutant gene alleles (FAD2 and FAD3) and may have superior oil fatty acid profile than any of the single mutant plants.

The current invention shows that since the gene locus BjFAD2-b is missing from its genome, the gene locus BjFAD2-a is the only functional FAD2 gene in B. juncea line J96D-4830. The MJ02-313-1/BjFAD2-a mutant allele abolishes expression of normal function of FAD2 in line MJ02-313-1 and the MJ02-357-3/BjFAD2-a mutant allele abolishes expression of normal function of FAD2 in line MJ02-357-3. However, both mutant lines MJ02-313-1 and MJ02-357-3 contain a considerable amount of linoleic acid and linolenic acid, which may suggest the synthesis of linoleic acid and linolenic acid by chloroplast desaturases, such as FADE and FAD7, are exported out of the chloroplasts.

In some embodiments, the stearic acid content may not increase in plants of the invention as a consequence of oleic acid increases. This is for example a characteristic of mutant line MJ02-313-1 and MJ02-357-3. In fact, the level of seed stearic acid is lower in line MJ02-313-1 and MJ02-357-3 than that in J96D-4830 (Table 3). This suggests that in both line MJ02-313-1 and MJ02-357-3, the sequential conversion of stearic acid to oleic acid, then to linoleic acid and linolenic acid in chloroplasts is enhanced, putatively to compensate for the deficiency in FAD2 activity in cytoplasm due to the MJ02-313-1/BjFAD2-a allele or MJ02-357-3/BjFAD2-a allele. Accordingly, in one aspect, the invention provides plants in which there is a decrease in stearic acid export out of chloroplast. In another aspect, the invention provides plants, such as the B. juncea lines MJ02-313-1 and MJ02-357-3 and their progeny thereof, having lower total saturates than plants that have an active FAD2 gene. In alternative embodiments, other Brassica species including B. juncea, B. napus and B. nigra may be provided with this characteristic.

In one aspect, the invention provides plants having a stable, heritable high oleic acid phenotype in both mutant lines MJ02-313-1 and MJ02-357-3. For example, the high oleic acid phenotype resulting from the mutant allele MJ02-313-1/BjFAD2-a and MJ02-357-3/BjFAD2-a is genetically heritable through $M_2$, $M_3$, and $M_4$ generations.

In various aspects, the invention involves the modulation of the number of copies of an expressible coding sequence in a plant genome. By "expressible" it is meant that the primary structure, i.e. sequence, of the coding sequence indicates that the sequence encodes an active protein. Expressible coding sequences may nevertheless not be expressed as an active protein in a particular cell. This 'gene silencing' may for example take place by various mechanisms of homologous transgene inactivation in vivo. Homologous transgene inactivation has been described in plants where a transgene has been inserted in the sense orientation, with the unexpected result that both the gene and the transgene were down-regulated (Napoli et al., 1990 Plant Cell 2: 279-289). The exact molecular basis for such co-suppression is unknown, although there are at least two putative mechanisms for inactivation of homologous genetic sequences. Transcriptional inactivation via methylation has been suggested as one mechanism, where duplicated DNA regions signal endogenous mechanisms for gene silencing. A post-transcriptional mechanism has also been suggested, where the combined levels of expression from both the gene and the transgene are thought to produce high levels of transcript which trigger threshold-induced degradation of both messages (van Bokland et al., 1994, Plant J. 6: 861-877). In the present invention, the expressible coding sequences in a genome may accordingly not all be expressed in a particular cell. For example, in some embodiments the FAD2 gene from only one of the two FAD2 loci in the amphidiploid B. juncea genome is expressible, and of the two expressible coding sequences at that locus only one may actually be expressed in a particular cell.

In alternative embodiments, the invention provides Brassica juncea plants wherein the activity of a fatty acid desaturase is altered or the oleic acid content is altered relative to wild type B. juncea that was used for the mutagenesis experiment. By fatty acid desaturase, it is meant that a protein exhibits the activity of introducing a double bond in the biosynthesis of a fatty acid. For example, FAD2 enzymes may be characterized by the activity of introducing the second double bond in the biosynthesis of linoleic acid from oleic acid. Altered desaturase activity may include an increase, reduction or elimination of a desaturase activity compared to a reference plant, cell or sample.

In other aspects, reduction of desaturase activity may include the elimination of expression of a nucleic acid sequence that encodes a desaturase, such as a nucleic acid sequence of the invention. By elimination of expression, it is meant herein that a functional amino acid sequence encoded by the nucleic acid sequence is not produced at a detectable level. Reduction of desaturase activity may include the elimination of transcription of a nucleic acid sequence that encodes a desaturase, such as a sequence of the invention encoding a FAD2 enzyme. By elimination of transcription it is meant herein that the mRNA sequence encoded by the nucleic acid sequence is not transcribed at detectable levels. Reduction of desaturase activity may also include the production of a truncated amino acid sequence from a nucleic acid sequence that encodes a desaturase. By production of a truncated amino acid sequence it is meant herein that the amino acid sequence encoded by the nucleic acid sequence is missing one or more amino acids of the functional amino acid sequence encoded by a wild type nucleic acid sequence. In addition, reduction of desaturase activity may include the production of a variant desaturase amino acid sequence. By production of a variant amino acid sequence it is meant herein that the amino acid sequence has one or more amino acids that are different from the amino acid sequence encoded by a wild type nucleic acid sequence. The current invention discloses that both mutant lines MJ02-313-1 and MJ02-357-3 produce FAD2 enzyme with variant amino acids compared to the wild type line J96D-4830. A variety of types of mutation may be introduced into a nucleic acid sequence for the purpose of reducing desaturase activity, such as frame-shift mutations, substitutions and deletions. For example, mutations in coding sequences may be made so as to introduce substitutions within functional motifs in a desaturase, such as the motif comprising three-histidine amino acid residues at amino acids 105-110, 141-145, and 316-320 of the FAD2 enzyme.

In some embodiments, the invention provides new FAD2 polypeptide sequences, which may be modified in accordance with alternative embodiments of the invention. It is well known in the art that some modifications and changes can be made in the structure of a polypeptide without substantially altering the biological function of that peptide to obtain a biologically equivalent polypeptide. As used herein, the term "conserved amino acid substitutions" refers to the substitution of one amino acid for another at a given location in the peptide, where the substitution can be made without any appreciable loss or gain of function, to obtain a biologically equivalent polypeptide. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Conversely, as used herein, the term "non-conserved amino acid substitutions" refers to the substitution of one amino acid for another at a given location in the peptide, where the substitution causes an appreciable loss or gain of function of the peptide, to obtain a polypeptide that is not biologically equivalent.

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). Non-conserved amino acid substitutions may be made where the hydrophilicity value of the residues is significantly different, e.g. differing by more than 2.0. For example, on this basis, the following amino acid substitutions for the wild type His (−0.5) at a position corresponding to amino acid 105 in BjFAD2-a would be non-conserved substitutions: Trp (−3.4), Arg (+3.0); Lys (+3.0); Asp (+3.0); Glu (+3.0). On this basis, the Glycine-94 Aspartic acid (G94A) mutation in enzyme BjFAD2-a of the line MJ02-313-1, as disclosed in the current invention, would be a non-conserved substitution.

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Non-conserved amino acid substitutions may be made where the hydropathic index of the residues is significantly different, e.g. differing by more than 2.0. For example, on this basis, the following amino acid substitutions for the wild type His (−3.2) at a position corresponding to amino acid 105 in BjFAD2-a would be non-conserved substitutions: Ile (+4.5); Val (+4.2); Leu (+3.8); Phe (+2.8); Cys (+2.5); Met (+1.9); Ala (+1.8); Gly (−0.4); Thr (−0.7); Ser (−0.8); and Trp (−0.9). On this basis, the Proline-216 Leucine (P216L) mutation in enzyme BjFAD2-a of the line MJ02-357-3, as disclosed in the current invention, would be a non-conserved substitution.

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. Non-conserved amino acid substitutions may be made where the residues do not fall into the same class, for example substitution of a basic amino acid for a neutral or non-polar amino acid. On this basis, the Glycine-94 Aspartic acid (G94A) mutation in enzyme BjFAD2-a of the line MJ02-313-1, as disclosed in the current invention, would be a non-conserved substitution.

It is understood that various modifications and alternatives can be made to the present invention. Certain specific embodiments thereof are described in the general methods and further explained by the following examples. The invention certainly applies to all canola quality *B. juncea* species as well as all non-canola quality *B. juncea* species. The invention may be applied to all other *Brassica* species including *B. juncea, B. nigra*, and *B. carinata*, to produce substantially similar results. It should also be understood that the following examples are not intended to limit the invention to particular forms disclosed, but instead, the invention is to cover all modifications, equivalents and alternatives falling within the scope of the invention.

EXAMPLES

Example 1

Creation of a Collection of Mutagenized *B. juncea* Seed Lines

Seeds of *Brassica juncea* line J96D-4830 were selected as the starting material. This line possess an endogenous edible oil with a fatty acid profile identical to that of canola oil, therefore it belongs to the family of canola quality *Brassica juncea* (CQBJ).

The J96D-4830 seeds from several self-pollinated individual plants were pooled and 3000 seeds were subjected to mutagenesis using ethylmethanesulfonate (EMS), a chemical mutagen. More specifically, the seeds were placed in a large petri dish containing 50 ml of 0.3% ethylmethanesulfonate (EMS) water solution. The petri dish was then covered by aluminum foil and incubated at 20° C. for 19 hrs with occasional gentle shaking. At the end of the incubation period, the EMS solution was collected into a bottle and neutralized with $Na_2CO_3$. The EMS treated seeds were washed 5 times with water before being planted into soil (Ready-Earth) in 6 flats, with each flat being divided into 20 rows (25 seeds/row×20 rows/flat=500 seeds/flat). The trays were covered with transparent plastic lids until completion of seed germination. The seeds were germinated in an environmentally-controlled greenhouse, which was maintained at 25° C./15° C., 14 hr/10 hr cycles of day/night conditions.

Six days after planting, the germinated seedlings were counted to determine the germination rate. Approximately 1600 out of 3000 EMS treated seeds were germinated to produce M1 plants (53%). All seedlings of these M1 plants were kept in the same greenhouse under the same conditions described above for another 2-3 weeks until the seedlings were transferred individually to 4"×4" pots (Kord Products Inc.). Slow-release fertilizer was included in the soil mixture. Due to limited greenhouse space, only 1350 plants were transferred (15 pots/tray×90 trays). The rest of the seedlings were discarded. The transplanted M1 plants were kept in the same growth conditions and bagged individually at flowering for self-pollination. After flowering, the lower leaves of these M1 plants were cut off for easier maintenance and were watered every day until harvesting.

Approximately 680 M1 plants produced M2 seeds. These M2 seeds were harvested from each individual plant, cleaned and packed individually and cataloged. Each M2 seed line has been named systematically as MJ02-001 to MJ02-680, respectively. These M2 seeds were kept under dry and cool conditions until a sub-sample of seeds from each line were planted in the greenhouse and leaf tissues were collected from each plant for total fatty acid extraction. Extracted total fatty acids were analyzed for composition profiles by gas liquid chromatography. Detailed screening procedures are described in Example 2.

Example 2

Screening for the Increased Oleic Acid Mutant phenotype

After the M2 seeds germinated, leaf tissue of the young seedlings was used for total fatty acid extraction. Analysis by gas liquid chromatography of fatty acid profiles of leaf tissues was used as a primary screening for mutant lines with increased oleic acid content. Although leaf tissue has a very different fatty acid composition than seed, we assume that there is a positive correlation between the two tissues in their fatty acid composition. In the present example, it was demonstrated that in *Brassica juncea*, the oleic acid content in leaves and the oleic acid content in seeds were positively correlated.

Eight seeds from each individual M2 seed line were planted in 2.5"×2.5" soil-containing pots to produce M2 plants. These M2 plants were kept in an environmentally-controlled greenhouse having 25° C./15° C., 14 hr/10 hr cycles of day/night conditions. After about 4 weeks when the M2 plants reached 4-5 leaf stages, ~0.1 g of the first leaf from each plant was collected and placed into a plastic vial containing a stainless metal rod (Profast'ners, Saskatoon, Saskatchewan). For total fatty acids extraction, 1 ml of 0.5 M sodium methoxide in methanol (Fisher, Nepean, Ontario) and 0.5 ml of hexane were added to each vial. The vials were capped well and shaken for 10 min at high speed using an Eberback Shaker (Eberback, Ann Arbour, Mich.). After tissue homogenization, the vials were kept at room temperature for an additional 20 min for oil extraction. Then 1 ml of distilled water was added to each vial followed by centrifugation of vials for 5 min at 3500 rpm using a Baxter Canlab Megafuge 1.0 (Heraeus Instruments). After centrifugation, 100 ul of the top hexane layer was transferred into an insert of the autosampler vial. Two micro liters of this sample preparation were then injected for analysis of fatty acid composition by gas liquid chromatography (GLC).

The GLC analysis was accomplished with a Hewlett Packard 5890 gas liquid chromatograph equipped with a DB-23 column (0.25-mm inner diameter×30-m length; Hewlett Packard) and a flame ionization detector. For the GLC operation the injector temperature was 250° C. and the detector temperature 300° C. The column temperature was initially held at 160° C. for 0.5 min and gradually increased to 245° C. in a linear gradient fashion at the rate of 10° C./min. The column temperature was then held at 245° C. for additional 4 min. Helium was used as a carrier gas with flow rate of 1 ml/min. The eluted fatty acid methyl esters were integrated and quantified based on area of each peak. The identity of each peak was confirmed by comparison with the following standards (Sigma): palmitic acid (16:0), palmitoleic acid (16:1), stearic acid (18:0), oleic acid (18:1, Δ9), cis-vaccenic acid (18:1, Δ1), linoleic acid (18:2), linolenic acid (18:3), arachidic acid (20:0), cis-11 eicosenoic acid (20:1), cis-11, 14 eicosadinoic acid (20:2), docosanoic acid (22:0), erucic acid (22:1), cis-13, 16 docosadienoic acid (22:2), tetracosanoic acid (24:0) and cis-15 tetracosenoic acid (24:1). Fatty acid profiles were expressed as percentage of individual fatty acid in total identified fatty acids.

In the previous patent application (US Patent Publication No. 2005/0039233, published Feb. 17, 2005), the high oleic acid *B. juncea* line MJ02-086-3 was disclosed. As the screening effort continued, two additional high oleic acid *B. juncea* lines, MJ02-313-1 and MJ02-357-3 were discovered. As shown in Table 2, line MJ02-313-1 contains 13.38% oleic acid and line MJ02-357-3 contains 17.74% oleic acid in total fatty acids extracted from leaf tissues. By contrast, the average of control plants contain 4.69% oleic acid in total leaf fatty acids. The data also show that there are corresponding decreases in linoleic acid content in high oleic acid lines compared to the average of controls. Other fatty acids remained virtually unchanged. The data shows that the conversion of oleic acid (18:1) to linoleic acid (18:2) is impaired in high oleic acid mutant lines, suggesting that MJ02-313-1 and MJ02-357-3 each possess a mutation in FAD2 genes.

TABLE 2

Fatty Acid Compositions of Leaf Tissues of Selected Mutant Lines, MJ02-313-1 (M2) and MJ02-357-3 (M2), During Initial Screening.

| Fatty Acids | Composition (%) | | |
|---|---|---|---|
| | MJ02-313-1 | MJ02-357-3 | Average of Control |
| 16:0 | 13.26 | 13.76 | 15.15 |
| 16:1 (cis-9) | 0.55 | 0.83 | 0.51 |
| 18:0 | 2.40 | 2.56 | 2.94 |
| 18:1 (cis-9) | 13.38 | 17.74 | 4.69 |
| 18:2 (cis-9, 12) | 9.03 | 9.66 | 14.23 |
| 18:3 (cis-9, 12, 15) | 49.94 | 44.72 | 49.74 |
| 20:0 | 0.45 | 0.19 | 0.39 |
| 20:1 | 0.41 | 0.35 | 0.18 |
| 20:2 | 0.27 | 0.15 | 0.17 |
| 22:0 | 0.15 | 0.16 | 0.27 |
| 22:1 (cis-13) | nd | nd | nd |
| 22:2 | nd | nd | 0.36 |
| 24:0 | 0.38 | 0.38 | 0.41 |
| 24:1 | 0.22 | 0.19 | 0.32 |

Note:
The value for the average of control is from multiple data points collected from leaf tissues of non-mutant plants (n = 88).
nd represents non-detectable.

Example 3

Confirmation of High Oleic Acid *Brassica juncea* Lines

After the initial leaf fatty acid screening, the potential mutant *B. juncea* lines, line MJ02-313-1 (M2) and line MJ02-357-3 (M2), were each transferred to a 6" planting pot and bagged before flowering to allow self-pollination and kept in the same growth conditions as described above. There was no abnormal growth or developmental behavior observed during the entire growth period in respect to leaf size and shape, flowering time, plant height and seed set. After seeds (M3) of each line were harvested, seed oil quality was evaluated for fatty acid compositions using a standard protocol recommended by the Canadian Grain Commission, Grain Research Laboratory. This protocol has been accepted by many international agencies including the Western Canada Canola/Rapeseed Recommending Committee (WCC/RCC). In this protocol, fatty acid methyl esters were prepared directly on crushed seeds followed by analysis by gas liquid chromatography in a similar way as described for leaf tissue. Specifically, for fatty acid extraction, one small scoop of seeds (approximately 300 mg or approximately 80 seeds) was placed into a plastic vial that contained a stainless metal rod (Profast'ners, Saskatoon, Saskatchewan). To each vial, 2 ml of 0.5 M sodium methoxide in methanol (Fisher, Nepean, Ontario) and 1 ml of hexane were added. The vial was capped well and shaken for 10 min at high speed using an Eberback Shaker (Eberback, Ann Arbour, Mich.). After tissue homogenization, the vials were kept at room temperature for an additional 20 min for oil extraction. Then 1 ml of distilled water was added to each vial followed by centrifugation of vials for 5 min at 3500 rpm using a Baxter Canlab Megafuge 1.0 (Heraeus Instruments). After centrifugation, 100 µl of the top hexane layer was transferred into an auto-sampler vial, to which an additional 400 µl of pure hexane was added. One micro-liter of this sample was then injected for fatty acid composition analysis by gas liquid chromatography (GLC) under the operating conditions described above.

Seed fatty acid analysis results confirmed the high oleic acid phenotype of line MJ02-313-1 (M3) and line MJ02-357-3 (M3) as well as line MJ02-86-3 (Table 3). The data show that the oleic acid content in the mutant line MJ02-313-1 is 83.35% compared to ~60% oleic acid content in the original DH line J96D-4830. Similarly, the oleic acid content in the mutant line MJ02-357-3 is 78.44% compared to ~60% oleic acid content in the original DH line J96D-4830. The data also show that there are corresponding decreases in linoleic acid and linolenic acid in both mutant lines in comparison with the control. Other fatty acids remain virtually unchanged. Seed fatty acid analysis results confirmed leaf tissue fatty acid analysis. Indeed, *B. juncea* lines MJ02-313-1, MJ02-357-3 and MJ02-86-3 are high oleic acid mutant lines. Consistency between the fatty acid results of leaf tissue and seed analysis demonstrates that the method of screening fatty acid composition using leaf tissues to predict fatty acid composition in oilseeds is efficient and accurate. This screening method is better than the half-seed screening method because it is simple and labor saving. It is also noteworthy that the mutations that cause inactivation/down regulation of FAD2 in lines MJ02-313-1 and MJ02-357-3 are likely recessive. Therefore, the MJ02-313-1 and MJ02-357-3 and their self-pollinated progenies should be homozygous for the mutant gene allele. To confirm the mutant gene homozygosity M3 seeds of MJ02-313-1 and MJ02-357-3 were planted again in the greenhouse and fatty acids extracted from leaf tissue were analyzed from 30 individual plants. The results show that all individual plants possess the mutant phenotype, i.e. significantly higher oleic acid content than the wild type line J96D-4830 (Table 4). These individual M3 plants were each bagged to allow self-pollination to produce M4 seeds.

TABLE 3

Seed Fatty Acid Compositions of Mutant Lines MJ02-313-1 (M3), MJ02-357-3 (M3) and MJ02-86-3 (M3).

| | Composition (%) | | | |
|---|---|---|---|---|
| Fatty Acid | MJ02-313-1 | MJ02-357-3 | MJ02-86-3 | J96D-4830 |
| 16:0 | 3.69 | 3.43 | 3.61 | 3.75 |
| 16:1 (cis-9) | 0.61 | 0.40 | 0.30 | 0.21 |
| 18:0 | 1.39 | 1.05 | 1.59 | 2.79 |
| 18:1 (cis-9) | 83.35 | 78.44 | 73.78 | 60.72 |
| 18:2 (cis-9, 12) | 1.81 | 3.96 | 8.65 | 16.72 |
| 18:3 (cis-9, 12, 15) | 5.24 | 9.34 | 9.41 | 11.97 |
| 20:0 | 0.53 | 0.40 | 0.44 | 0.76 |
| 20:1 | 1.75 | 1.65 | 1.25 | 1.43 |
| 20:2 | 0.07 | 0.07 | nd | nd |
| 22:0 | 0.32 | 0.21 | 0.22 | 0.56 |
| 22:1 (cis-13) | 0.08 | 0.06 | nd | nd |
| 22:2 | nd | nd | nd | nd |
| 24:0 | 0.46 | 0.31 | 0.25 | 0.27 |
| 24:1 | 0.57 | 0.54 | 0.38 | 0.46 |
| Total Sat | 6.45 | 5.46 | 6.11 | 8.13 |

The value of J96D-4830 is an average of 6 independent analysis all showing the similar trend.
nd represents non-detectable.

TABLE 4

Fatty Acid Compositions of Leaf Tissues from Individual Plants of the Selected Mutant Lines MJ02-313-1 (M3) and MJ02-357-3 (M3).

| | Composition (%) | | |
|---|---|---|---|
| Fatty Acid | MJ02-313-1 | MJ02-357-3 | J96D-4830 |
| 16:0 | 17.06 ± 1.19 | 14.31 ± 1.07 | 17.30 ± 1.14 |
| 16:1 (cis-9) | 0.52 ± 0.21 | 0.55 ± 0.04 | 0.47 ± 0.09 |
| 18:0 | 11.24 ± 2.72 | 7.46 ± 1.75 | 7.11 ± 1.02 |
| 18:1 (cis-9) | 15.98 ± 1.72 | 13.51 ± 1.79 | 7.51 ± 1.71 |
| 18:2 (cis-9, 12) | 5.01 ± 0.35 | 5.16 ± 0.36 | 13.32 ± 1.46 |
| 18:3 (cis-9, 12, 15) | 45.76 ± 4.33 | 44.80 ± 3.15 | 49.04 ± 3.55 |
| 20:0 | 0.62 ± 0.11 | 0.68 ± 0.09 | 0.72 ± 0.13 |
| 20:1 | 0.27 ± 0.07 | 0.43 ± 0.15 | 0.22 ± 0.04 |
| 20:2 | 0.08 ± 0.04 | 1.80 ± 1.84 | 0.15 ± 0.02 |
| 22:0 | 0.42 ± 0.25 | 0.58 ± 0.34 | 0.34 ± 0.11 |
| 22:1 (cis-13) | 0.20 ± 0.13 | 1.75 ± 0.76 | 0.69 ± 1.16 |
| 22:2 | nd | 1.84 ± 0.37 | 0.52 ± 0.61 |
| 24:0 | 0.73 ± 0.15 | 1.11 ± 0.39 | 0.55 ± 0.08 |
| 24:1 | 0.26 ± 0.10 | 0.52 ± 0.70 | 0.31 ± 0.18 |

Note:
Leaf tissue samples from individual plant (M3) of selected mutant lines were analyzed for fatty acid composition for confirmation of genetic homozygosity.
Values of MJ02-313-1 are means ± SD; n = 30; Values of MJ02-357-3 are means ± SD; n = 30; Values of J96D-4830 are means ± SD; n = 4.
nd represents non-detectable.

Example 4

Genotyping of the Mutant Lines MJ02-313-1 and MJ02-357-3

For mutagenesis of *B. juncea*, the breeding line J96D-4830 was used. The genotype of J96D-4830 was known from earlier studies. Techniques are available to distinguish canola *Brassica juncea* (~60% oleic acid) from low erucic/low oleic acid *Brassica juncea* (~45% oleic acid) by examining the presence of the BjFAD2-b gene (U.S. Patent Publication No. 20030221217, Yao et al; incorporated herein by reference).

Since the BjFAD2-b gene locus is deleted from the J96D-4830 genome (FIG. 1), sequence comparisons were focused on the other FAD2 gene locus, BjFAD2-a, when the mutant lines MJ02-313-1 and MJ02-357-3 were analyzed.

Leaf genomic DNA extraction methods and PCR conditions for this analysis are briefly described herein. Genomic DNA was isolated from leaf tissues as described previously (Dellaporta et al., Plant Mol. Biol. Rep. 1: 19-21, 1983). For direct genomic PCR, 100 ng of genomic DNA was used in a total volume of 50 µl containing 5 µl of 10× Taq DNA polymerase buffer with MgCl$_2$ (Invitrogen) and 2 units of Taq DNA polymerase, 0.25 µM each of primers FAD2Pup-1 (5'-GAAGCCAAGCACGATCCTCC-ATT-3') (SEQ ID NO:8) and 2BR4 (5'-ACACGCTTGAGGGTATCGGTTTC-3') (SEQ ID NO:9) and 50 µM of each dNTP. The amplification was done with 35 cycles of 1 min at 94° C., 1 min at 56° C. and 2 min at 72° C. The PCR products were electrophoresed on 1% agarose gel in TAE running buffer with the 1 Kb plus DNA ladder (BRL) as DNA size marker.

As shown in FIG. 1, using this approach, it was confirmed that both BjFAD2-b and BjFAD2-a genes are present in the original low erucic/low oleic acid *Brassica juncea* lines (J92D-1356, J98D-8124 and J99D-8400). However, the BjFAD2-b gene is missing from the canola *Brassica juncea* lines (J96D-4830, J96D-0889 and J98D-1384).

To identify the mutation in lines MJ02-313-1 and MJ02-357-3, the entire BjFAD2-a gene was cloned and sequenced from each mutant line. For this purpose, leaf genomic DNA, isolated from both mutant line MJ02-086-3 and line J96D-4830, were used as the PCR template. PCR primers FAD2Pup-1 (5'-GAAGCCAAGCACGATCCTCCATT-3') (SEQ ID NO:8) and FAD2low (5'-TCATAACTTATTGTTG-TACCAG-3') (SEQ ID NO:10), were used to amplify the entire BjFAD2-a gene. For PCR, 100 ng of genomic DNA was used in a total volume of 50 µl containing 5 ml of 10× Taq DNA polymerase buffer with MgCl$_2$ (Invitrogen) and 2 units of Taq DNA polymerase, 0.25 µM each of primers FAD2Pup and FAD2low and 50 µM of each dNTP. The amplification was done with 35 cycles of 1 min at 94° C., 1 min at 56° C. and 2 min at 72° C. The PCR products were electrophoresed on 1% agarose gel in TAE running buffer with the 1 Kb plus DNA ladder (BRL) as DNA size marker. The results show that a single PCR fragment (~2.9 kb in size) was amplified from both lines, which is the expected size of BjFAD2-a gene fragment including the 5' end of the gene promoter and the 3' end of ORF of the BjFAD2-a gene (U.S. patent publication No. 2003/0221217). The PCR fragments were cloned into pCR®4-TOPO cloning vectors (Invitrogene, Burlington, ON). The inserts were completely sequenced. Comparison of sequences indicated that the BjFAD2-a gene of line MJ02-313-1 has a single basepair G to A substitution in the ORF at position 281 in reference to the first ATG start codon. (FIG. 2 and FIG. 3). The mutation changes the codon GGC (Glycine) of line J96D-4830 to GAC (Aspartic acid) in line MJ02-313-1. We designate the mutant allele MJ02-313-1/BjFAD2-a, and the wild type allele J96D-4830/BjFAD2-a. The changed amino acid residue is in the 94$^{th}$ position in reference to the first Methionine and is therefore termed G94D mutation (FIG. 5).

Similarly, comparison of sequences indicated that the BjFAD2-a gene of line MJ02-357-3 has a single basepair "C" to "T" substitution in the ORF at position 647 in reference to the first ATG start codon. (FIG. 2 and FIG. 4). The mutation changes the codon CCC (Proline) of line J96D-4830 to CTC (Leucine) in line MJ02-357-3. We designate the mutant allele MJ02-357-3/BjFAD2-a. The changed amino acid residue is in the 216$^{th}$ position in reference to the first Methionine and is therefore termed P216L mutation (FIG. 5).

Metabolite analysis shows that in seed the increase in oleic acid in the mutant line MJ02-313-1 is accompanied by a corresponding decrease in linoleic acid (from 16.72% to 1.81%) and a decrease in linolenic acid (from 11.97% to 5.24%). Similarly, the increase in oleic acid in mutant line seed of MJ02-357-3 also is accompanied by a corresponding decrease in linoleic acid (from 16.72% to 3.96%) and a decrease in linolenic acid (from 11.97% to 9.34%). These data support the genotyping data that MJ02-313-1 and MJ02-357-3 are mutant lines with mutant FAD2 gene alleles.

Alternative aspects of the invention make it possible that a single plant can have both FAD2 and FAD3 mutations combined. For example by genetic crosses using MJ02-313-1 or MJ02-357-3 as one parent plant with another parent plant with a FAD3 gene mutation followed by selecting progenies based on their fatty acid profile or genetic markers. In this specific embodiment, the FAD2 and FAD3 double mutant lines are high oleic acid and low in linolenic acid.

Since the BjFAD2-a is the only functional FAD2 gene locus in line J96D-4830, the MJ02-313-1/BjFAD2-a mutant allele and the MJ02-357-3/BjFAD2-a mutant allele abolish the expression of functional FAD2 or significantly reduce the FAD2 activity in the corresponding mutant lines. However, both mutant lines MJ02-313-1 and MJ02-357-3 still contain a considerable amount of linoleic acid and linolenic acid, which are required to maintain the normal function of plant membranes. It is also possible that the considerable amount of linoleic acid and linolenic acid are synthesized in chloroplasts by other fatty acid desaturases, such as FAD6 and FAD7, and exported out from the chloroplasts.

As evidenced by metabolite analysis, in some embodiments, the stearic acid content of mutant plants of the invention does not increase although oleic acid increases. Instead, both leaf and seed stearic acid contents are lower in mutant lines than those in J96D-4830 (Tables 2 and 3). Accordingly, one aspect the invention provides plants, such as *Brassica juncea* lines MJ02-313-1 and MJ02-357-3, that have lower total saturates than wild-type plants. Therefore, the mutant gene alleles of the current invention provide a valuable tool to reduce total saturates in oil.

FURTHER EMBODIMENTS OF THE INVENTION

With the advent of molecular biology techniques that have allowed the isolation and characterization of genes that encode specific protein products, scientists in the field of plant biology developed a strong interest in engineering the plant genome to contain and express foreign or additional genes, or to express modified versions of native, genes (perhaps driven by different promoters) in order to alter the traits of a plant in a specific manner. Such foreign additional and/or modified genes are referred to herein collectively as "transgenes". Over the last ~20 years several methods for producing transgenic plants have been developed for various crops, which include *Agrobacterium*-mediated transformation and particle bombardment. For specific *Brassica* transformation protocols see for reference to patents (U.S. Pat. No. 5,188,958 issued to Moloney et al., Feb. 23, 1993; U.S. Pat. No. 6,051,756 issued to Chen et al., Apr. 18, 2000; U.S. Pat. No. 6,297,056 issued to Tulsieram et al., Oct. 2, 2001). The present invention, in particular embodiments, also relates to transformed versions of the claimed varieties or lines.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed *Brassica* plants, using transformation methods as described below to incorporate transgenes into the genetic material of the *Brassica* plant(s).

Expression Vectors for *Brassica* Transformation: Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, which, when under the control of plant regulatory signals confers resistance to kanamycin (Fraley et al., Proc. Natl. Acad. Sci. U.S.A., 80:4803, 1983). Another commonly used selectable marker gene is the hygromycin phosphotransferase gene which confers resistance to the antibiotic hygromycin (Vanden Elzen et al., Plant Mol. Biol., 5:299, 1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant (Hayford et al., Plant Physiol. 86:1216, 1988; Jones et al., Mol. Gen. Genet., 210:86, 1987; Svab et al., Plant Mol. Biol. 14:197, 1990; Hille et al., Plant Mol. Biol. 7:171, 1986). Other selectable marker genes confer resistance to herbicides such as glyphosate, glufosinate or bromoxynil (Comai et al., Nature 317:741-744, 1985; Gordon-Kamm et al., Plant Cell 2:603-618, 1990; Stalker et al., Science 242:419-423, 1988).

Other selectable marker genes for plant transformation not of bacterial origin include, for example, mouse dihydrofolate reductase, plant 5-enol-pyruvyl-shikimate-3-phosphate synthase and plant acetolactate synthase (Eichholtz et al., Somatic Cell Mol. Genet. 13:67, 1987; Shah et al., Science 233:478, 1986; Charest et al., Plant Cell Rep. 8:643, 1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., Plant Mol. Biol. Rep. 5:387, 1987; Teed et al., EMBO J. 8:343, 1989; Koncz et al., Proc. Natl. Acad. Sci. U.S.A. 84:131, 1987; DeBlock et al., EMBO J. 3:1681, 1984).

In vivo methods for visualizing GUS activity that do not require destruction of plant tissue are available (Molecular Probes publication 2908, IMAGENE GREEN, p. 1-4, 1993; and Naleway et al., J. Cell Biol. 115:151a, 1991). However, these in vivo methods for visualizing GUS activity have not proven useful for recovery of transformed cells because of low sensitivity, high fluorescent backgrounds and limitations associated with the use of luciferase genes as selectable markers. A gene encoding Green Fluorescent Protein (GFP) has been utilized as a marker for gene expression in prokaryotic and eukaryotic cells (Chalfie et al., Science 263:802, 1994). GFP and mutants of GFP may be used as selectable markers.

Promoters—Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

Inducible Promoters—An inducible promoter is operably linked to a gene for expression in *Brassica*. Optionally, the inducible promoter is operably linked to a nucleotide sequence encoding a signal sequence which is operably linked to a gene for expression in *Brassica*. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., PNAS 90:4567-4571, 1993); In2 gene from maize which responds to benzenesulfonamide herbicide safeners (Hershey et al., Mol. Gen. Genetics 227:229-237 (1991) and Gatz et al., Mol. Gen. Genetics 243:32-38 (1994)) or Tet repressor from Tn10 (Gatz et al., Mol. Gen. Genetics 227: 229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., Proc. Natl. Acad. Sci. U.S.A. 88:0421 (1991)).

Constitutive Promoters—A constitutive promoter is operably linked to a gene for expression in *Brassica* or the constitutive promoter is operably linked to a nucleotide sequence encoding a signal sequence which is operably linked to a gene for expression in *Brassica*.

Many different constitutive promoters can be utilized in the instant invention. Exemplary constitutive promoters include, but are not limited to, the promoters from plant viruses such as the 35S promoter from CaMV (Odell et al., Nature 313:810-812, 1985) and the promoters from such genes as rice actin (McElroy et al., Plant Cell 2:163-171, 1990); ubiquitin (Christensen et al., Plant Mol. Biol. 12:619-632, 1989; Christensen et al., Plant Mol. Biol. 18:675-689 (1992); pEMU (Last et al., Theor. Appl. Genet. 81:581-588, 1991); MAS (Velten et al., EMBO J. 3:2723-2730, 1984); maize H3 histone (Lepetit et al., Mol. Gen. Genetics 231:276-285, 1992; Atanassova et al., Plant Journal 2 (3): 291-300, 1992).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

Tissue-specific or Tissue-preferred Promoters—A tissue-specific promoter is operably linked to a gene for expression in *Brassica*. Optionally, the tissue-specific promoter is operably linked to a nucleotide sequence encoding a signal sequence which is operably linked to a gene for expression in *Brassica*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992); Knox, C., et al., Plant Mol. Biol. 9:3-17 (1987); Lerner et al., Plant Physiol. 91:124-129 (1989); Fontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is a *Brassica* plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., Plant Mol. Biol. 24:25 (1994), who disclose the nucleotide sequences of several *Clivia miniata* mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec.

Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyper-accumulation of a monoterpene, a sesquiterpene, a steroid, a hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

L. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., Plant Sci 89:43 (1993), of heterologous expression of a cecropin B, a lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Intl Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonans. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by mutant 5-enolpyruvyl-shikimate-3-phosphate synthase (EPSPS) and aroA genes, respectively) and other phosphono compounds such as glufosinate (phosphinothricin acetyl transferase (PAT) and *Streptomyces hygroscopicus* PAT, bar, genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., Theor. Appl. Genet. 83:435 (1992).

C. An herbicide that inhibits photosynthesis, such as a triazine (psbA and gs+ genes) or a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992).

B. Decreased phytate content—1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., J. Bacteol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus lichenifonnis* α-amylase), Elliot et al., Plant Molec. Biol. 21:515 (1993) (nucleotide sequences of tomato invertase genes), Søgaard et al., J. Biol. Chem. 268:22480 (1993) (site-directed mutagenesis of barley α-amylase gene), and Fisher et al., Plant Physiol. 102:1045 (1993) (maize endosperm starch branching enzyme II).

Methods for *Brassica* Transformation—Numerous methods for plant transformation have been developed including biological and physical plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., Bio/Technology 9:996 (1991). Alternatively, liposome and spheroplast fusion have been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine has also been reported. Hain et al., Mol. Gen. Genet. 199:161 (1985) and Draper et al., Plant Cell Physiol. 23:451 (1982). Electroporation of protoplasts and whole cells and tissues have also been described. Donn et al., In Abstracts of VIIth International Congress on Plant Cell and Tissue Culture IAPTC, Δ2-38, p 53 (1990); D'Halluin et al., Plant Cell 4:1495-1505 (1992) and Spencer et al., Plant Mol. Biol. 24:51-61 (1994).

Following transformation of *Brassica* target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed with another (non-transformed or transformed) variety in order to produce a new transgenic variety. Alternatively, a genetic trait which has been engineered into a particular *Brassica* line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture of *Brassica*—Further production of the *B. juncea* lines, MJ02-313-1 and MJ02-357-3, can occur by self-pollination or by tissue culture and regeneration. Tissue culture of various tissues of *Brassica* and regeneration of plants therefrom is known. For example, the propagation of a *Brassica* cultivar by tissue culture is described in any of the following, but not limited to any of the following: Chuong et al., "A Simple Culture Method for *Brassica* Hypocotyl Protoplasts", Plant Cell Reports 4:4-6 (1985); Barsby, T. L., et al., "A Rapid and Efficient Alternative Procedure for the Regeneration of Plants from Hypocotyl Protoplasts of *Brassica napus*", Plant Cell Reports, (Spring, 1996); Kartha, K., et al., "In vitro Plant Formation from Stem Explants of Rape", Physiol. Plant, 31:217-220 (1974); Narasimhulu, S., et al., "Species Specific Shoot Regeneration Response of Cotyledonary Explants of Brassicas", Plant Cell Reports, (Spring 1988); Swanson, E., "Microspore Culture in *Brassica*", Methods in Molecular Biology, Vol. 6, Chapter 17, p. 159 (1990).

Thus, another aspect of this invention is to provide cells that upon growth and differentiation produce *Brassica* plants having the physiological and morphological characteristics of *B. juncea* lines of MJ02-313-1 and MJ02-357-3.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, siliques, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, described certain techniques, the disclosures of which are incorporated herein by reference.

Single Gene Conversion—When the term "*Brassica* plant" is used in the context of the present invention, this also includes any single gene conversions of that group. The term "single gene converted plant" as used herein refers to those *Brassica* plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9 or more times to the recurrent parent. The parental *Brassica* plant which contributes the gene for the desired characteristic is termed the "nonrecurrent" or "donor parent". This terminology refers to the fact that the nonrecurrent parent is used one time in the backcross protocol and therefore does not recur. The parental *Brassica* plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a *Brassica* plant is obtained wherein essentially all of the desired morphological and physiological characteristics of the recurrent parent are recovered in the converted plant, in addition to the single transferred gene from the nonrecurrent parent as determined at the 5% significance level when grown under the same environmental conditions.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are specifically hereby incorporated by reference.

This invention also is directed to methods for producing a *Brassica* plant by crossing a first parent *Brassica* plant with a second parent *Brassica* plant wherein the first or second parent *Brassica* plant is a *Brassica* plant of the MJ02-313-1 or MJ02-357-3. Thus, any such methods using the *Brassica juncea* line MJ02-313-1 or MJ02-357-3 are part of this invention: selfing, backcrosses, hybrid production, crosses to populations, and the like. All plants produced using *Brassica* line MJ02-313-1 or MJ02-357-3 as a parent are within the scope of this invention, including those developed from varieties derived from *Brassica* line MJ02-313-1 or MJ02-357-3. Advantageously, the *Brassica* variety could be used in crosses with other, different, *Brassica* plants to produce first generation ($F_1$) *Brassica* hybrid seeds and plants with superior characteristics. The variety of the invention can also be used for transformation where exogenous genes are introduced and expressed by the variety of the invention. Genetic variants created either through traditional breeding methods using line MJ02-313-1 or MJ02-357-3 or through transformation of line MJ02-313-1 or MJ02-357-3 by any of a number of protocols known to those of skill in the art are intended to be within the scope of this invention.

REFERENCES

The following documents are specifically incorporated herein by reference.

1. Agnihotri, A., Kaushik, N., Singh, N. K., Raney, J. P. and Downey, R. K. 1995. Selection for better agrononical and nutritional characteristics in Indian rapeseed-mustard. Proc. 9th Int. Rapeseed Cong., Cambridge, U.K. Vol. 2:425-427.
2. Ames, B. N. 1983. Dietary carcinogens and anticarcinogens. Science 221:1256-1264.
3. Daun, J. K. and McGregor, D. I. 1991. Glucosinolates in seeds and residues. In: Analysis of Oilseeds, Fats and Fatty foods. J. B. Rossell and J. L. R. Pritchard, eds. Elsevier Applied Science, London, pp. 185-226.
4. Downey, R. K. and Rakow, G. F. W. 1987. Rapeseed and mustard. In: Principles of cultivar development. W. R. Fehr, ed. Macmillian, N.Y. Pp. 437-486.
5. Eskin, N. A. M., Vaisey-Genser, M., Durance-Todd, S, and Przybylski, R. 1989. Stability of low linolenic acid canola oil to frying temperatures. J. Amer. Oil Chem. Soc. 66: 1081-1084.
6. Food Chemicals Codex. 1996. 4.sup.th Edition. Committee on Food Chemicals Codex, Food and Nutrition Board, Institute of Medicine, National Academy of Sciences. National Academy Press, Washington. pp. 77-79.

7. Kirk, J. T. O. and Oram, R. N. 1981. Isolation of erucic acid free lines of *Brassica juncea*: Indian mustard now a potential oilseed crop in Australia. J. Aust. Inst. Agric. Sci. 47:51-52.
8. Love, H. K., Rakow, G., Raney, J. P. and Downey, R. K. 1990. Development of low glucosinolate mustard. Can. J. Plant Sci. 70:419-424.
9. Love, H. K., Rakow, G., Raney, J. P. and Downey, R. K. 1991. Breeding improvements towards canola quality *Brassica juncea*. Proc. 8.sup.th Int. Rapeseed Congress, Saskatoon, Canada. Vol. 1:164-169.
10. McDonald, B. E. 1995. Oil properties of importance in human nutrition. In: *Brassica* Oilseeds: Production and Utilization. D. S. Kimber and D. I. McGregor, eds., CAB International, Oxon, U.K., pp. 291-299.
11. Potts et al., 1999. Canola-quality *Brassica juncea*, a new oilseed crop for the Canadian prairies. The proceedings of 10th International Rapeseed Congress in Sep. 26-29, 1999; Can berra, Australia; CD-ROM.
12. Potts and Males. 1999. Inheritance of fatty acid composition in *Brassica juncea*. The proceedings of 10th International Rapeseed Congress in Sep. 26-29, 1999; Can berra, Australia; CD-ROM.
13. Rakow, G. 1991. Canola quality mustard. Proc. Special Cropportunities I: A conference organized by the Crop Development Centre and the Extension Division, University of Saskatchewan, Saskatoon, Canada pp. 55-59.
14. Rakow, G., Raney, J. P. and Males, D. 1995. Field performance of canola quality *Brassica juncea* Proc. 9.sup.th Int. Rapeseed Congress, Cambridge, U.K. Vol. 2:428-430.
15. Raney, P., Rakow, G. and Olson, T. 1995. Development of zero erucic, low linolenic *Brassica juncea* utilizing interspecific crossing. Proc. 9.sup.th Int. Rapeseed Congress, Cambridge, U.K. Vol. 2:413-415.
16. Stotjesdijk et al., 1999. Genetic manipulation for altered oil quality in *Brassica*. The proceedings of 10th International Rapeseed Congress in Sep. 26-29, 1999; Can berra, Australia; CD-ROM.
17. Swanson, E. B., Coumans, M. P., Brown, G. L., Patel, J. D. and Beversdorf, W. D. 1988. The characterization of herbicide tolerant plants in *Brassica napus* L. after in vitro selection of microspores and protoplasts. Plant Cell Rep. 7:83-87.
18. Swanson, E. B., Herrgesell, M. J., Arnoldo, M., Sippell, D. W. and Wong, R. S.C. 1989. Microspore mutagenesis and selection: canola plants with field tolerance to the imidazolinones. Theor. Appl. Genet. 78:525-530.
19. Thiagarajah, M. R. and Stringham, G. R. 1993. A comparison of genetic segregation in traditional and microspore-derived populations of *Brassica juncea* L. Czem and Coss. Plant Breeding 111:330-334.
20. Woods, D. L., Capcara, J. J. and Downey, R. K. 1991. The potential of mustard (*Brassica juncea* (L.) Coss) as an edible oil crop on the Canadian Prairies. Can. J. Plant Sci. 71:195-198.

DEPOSIT INFORMATION

A deposit of the Saskatchewan Wheat Pool, Inc. proprietary *Brassica juncea* line MJ02-313-1 disclosed above and recited in the appended claims has been made with the American Type Culture Collection (ATCC), 10801 University Boulevard, Manassas, Va. 20110. The date of deposit was Oct. 27, 2006. The deposit of 2,500 seeds was taken from the same deposit maintained by Saskatchewan Wheat Pool, Inc. since prior to the filing date of this application. Upon allowance of any claims in this application all restrictions on the availability to the public of the variety will be irrevocably removed, and the deposit is intended to meet all of the requirements of 37 C.F.R. 1.801-1.809. The ATCC accession number is PTA-7955. The deposit will be maintained in the depository for a period of 30 years, or 5 years after the last request, or for the effective life of the patent, whichever is longer, and will be replaced as necessary during that period.

A deposit of the Saskatchewan Wheat Pool, Inc. proprietary *Brassica juncea* line MJ02-357-3 disclosed above and recited in the appended claims has been made with the American Type Culture Collection (ATCC), 10801 University Boulevard, Manassas, Va. 20110. The date of deposit was Oct. 27, 2006. The deposit of 2,500 seeds was taken from the same deposit maintained by Saskatchewan Wheat Pool, Inc. since prior to the filing date of this application. Upon allowance of any claims in this application all restrictions on the availability to the public of the variety will be irrevocably removed, and the deposit is intended to meet all of the requirements of 37 C.F.R. 1.801-1.809. The ATCC accession number is PTA-7956. The deposit will be maintained in the depository for a period of 30 years, or 5 years after the last request, or for the effective life of the patent, whichever is longer, and will be replaced as necessary during that period.

A deposit of the Saskatchewan Wheat Pool, Inc. proprietary *Brassica juncea* line MJ02-86-3 disclosed above and recited in the appended claims has been made with the American Type Culture Collection (ATCC), 10801 University Boulevard, Manassas, Va. 20110. The date of deposit was Jun. 22, 2004. The deposit of 2,500 seeds was taken from the same deposit maintained by Saskatchewan Wheat Pool, Inc. since prior to the filing date of this application. All restrictions upon the deposit have been removed, and the deposit is intended to meet all of the requirements of 37 C.F.R. 1.801-1.809. The ATCC accession number is PTA-6097. The deposit will be maintained in the depository for a period of 30 years, or 5 years after the last request, or for the effective life of the patent, whichever is longer, and will be replaced as necessary during that period.

CONCLUSION

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A *Brassica juncea* plant whose seeds have an endogenous fatty acid content comprising at least 70.0% oleic acid by weight, and less than 1.0% erucic acid by weight and whose seeds comprise a null mutant allele at the BjFAD2-a gene locus, wherein the BjFAD2-a allele comprises a single nucleotide mutation, and wherein the BjFAD2-b gene locus is deleted from the genome.

2. The *Brassica juncea* plant of claim 1 whose seeds have an endogenous fatty acid content comprising 70.0% to 84.0% oleic acid by weight, and less than 1.0% erucic acid by weight.

3. The *Brassica juncea* plant of claim 1, wherein the mutant allele codes for a mutation selected from the group consisting of: a premature truncation, a glycine to aspartic acid mutation at amino acid 94, and a proline to leucine mutation at amino acid 216.

4. The *Brassica juncea* plant according to claim 3, wherein said plant is line MJ02-357-3, wherein a representative sample of seed of MJ02-357-3 has been deposited under ATCC Accession No. PTA-7956.

5. The *Brassica juncea* plant according to claim 3, wherein said plant is a progeny plant of line MJ02-313-1, wherein a representative sample of seed of MJ02-313-1 has been deposited under ATCC Accession No. PTA-7955.

6. The *Brassica juncea* plant according to claim 3, wherein said plant is a progeny plant of MJ02-357-3, wherein a representative sample of seed of MJ02-357-3 has been deposited under ATCC Accession No. PTA-7956.

7. The *Brassica juncea* plant according to claim 3, wherein said plant is line MJ02-313-1, wherein a representative sample of seed of MJ02-313-1 has been deposited under ATCC Accession No. PTA-7955.

8. the *Brassica juncea* plant of claim 3, wherein the premature truncation occurs immediately after amino acid 100.

9. Seeds of the *Brassica juncea* plant according to any one of claims 1, 2, 7, 4, 5, 6, 3 and 8, wherein said seeds having total extractable oils comprising a fatty acid content of at least 70.0% oleic acid by weight, less than 10.0% linoleic acid by weight, less than 10.0% linolenic acid by weight, less than 2.5% stearic acid by weight and less than 1.0% erucic acid by weight.

10. The seeds of claim 9 having total extractable oils comprising a fatty acid content of
 a) an oleic acid content of 70.0% to 84.0% by weight
 b) a linoleic acid content of 1.5% to 10% by weight
 c) a linolenic acid content of 5.0% to 10% by weight
 d) a stearic acid content of 1.0% to 2.5% by weight
 e) an erucic acid of 0% to 1.0% by weight.

11. A *Brassica juncea* seed designated MJ02-313-1, representative sample of seed was deposited under ATCC Accession No. PTA-7955.

12. A *Brassica juncea* seed designated MJ02-357-3, representative sample of seed was deposited under ATCC Accession No. PTA-7956.

* * * * *

SEQUENCE LISTING

<160> NUMBER OF SEQ ID NOS: 10

<210> SEQ ID NO 1
<211> LENGTH: 2909
<212> TYPE: DNA
<213> ORGANISM: Brassica juncea

<400> SEQUENCE: 1

```
gatattttt taagttttt tctcacatgg gagaagaaga agccaagcac gatcctccat      60
tctcaacttt atagcatttt tttctttct ttccggctac cactaacttc tacagttcta     120
cttgtgagtc ggcaaggacg tttcctcata ttaaagtaaa gacatcaaat accataatct    180
taatgctaat taacgtaacg gatgagttct ataacacaac ccaaactagt ctttgtgaac    240
attaggattg ggtaaaccaa tatttacatt ttaaaaacaa aatacaaaaa gaaacgtgat    300
aaactttata aaagcaatta tatgatcacg gcatctttt cacttttccg taaatatata     360
taagtggtgt aaatatcaga tatttggagt agaaaaaaaa aaaaaaaaaa agaaatatga    420
agagaggaaa taatggaggg gcccactagt aaaaagaaa gaaagagat gtcactcaat      480
cgtctcacac gggcccccgt caatttaaac ggcctgcctt ctgcccaatc gcatcttacc    540
agaaccagag agattcatta ccaaagagat agagagagaa agagaggaga cagagagagt    600
ttgaggaggt gcttcttcgt agggttcatc gttattaacg ttaaatcttc atcccctac     660
gtcaaccagc tcaaggtccc tttcttcttc catttcctct catttttacg ttgttttcaa    720
tcttggtctg ttctttttctt atcgctttc tattctatct atcatttttg cttttcagtc    780
gatttaattc tagacctgtt aatatttatt gcattaaact atagatctgt tcttgattct    840
ctgtttctt gtgtgaaatc ttgatgctgt ctttaccatt aatctgatta tattgtctat     900
accttggaga atatgaaatg ttgcattttc atttgtccga atacaaactg tttgactttc    960
aatcttttt aatgatttat tttgatgggt tggtggagtt gaaaaatcac catagcagtc    1020
tcacgtcctg gtcttagaaa tatccttcct attcaaagtt atatatttt gtttacttgt    1080
cttagatctg gacctgagac atgtaagtac ctatttgttg aatctttggg taaaaaactt    1140
atgtctctgg gtaaaatttg cttggagatt tgaccgattc ctattggctc ttgattctgt    1200
aattacgtaa tacatgaaaa atgtttcatt tggcctatgc tcacttcatg cttataaact    1260
ttttcttgca aattaattgg attagatgct ccttcataga ttcagatgca atagatttgc    1320
atgaagaaaa taatagaatt catgatagta aaaagattgt atttttgttt gtttgtttat    1380
gtttaaaagt ctatatgttg acaatagagt tgctatcaac tgtttcattt aggtttatgt    1440
ttttgtcaag ttgcttattc taagagacat tgtgattatg acttgtcttc tctaacgtag    1500
tttagtaata aaagacgaaa gaaattgata tccacaagaa agagatgtaa gctgtaacgt    1560
atcaaatctc attaataact agtagtattc tcaacgctat cgtttatttc tttctttggt    1620
ttgccactat atgccgcttc tctcctcttt tgtcccacgt actatccatt tttttgaaac    1680
tttaataacg taacactgaa tattaatttg ttggtttaat taactttgag tttgtttttg    1740
gtttatgcag aaacatgggt gcaggtggaa gaatgcaagt gtctcctccc tcgaagaagt    1800
ctgaaaccga caccatcaag cgcgtaccct gcgagacacc gcccttcact gtcggagaac    1860
tcaagaaagc aatcccaccg cactgtttca aacgctcgat ccctcgctct ttctcctacc    1920
tcatctggga catcatcata gcctcctgct tctactacgt cgccaccact tacttcccctc    1980
tcctccctca ccctctctcc tacttcgcct ggcctctcta ctgggcctgc cagggctgcg    2040
```

-continued

```
tcctaaccgg cgtctgggtc atagcccacg agtgcggcca ccacgccttc agcgactacc   2100
agtggcttga cgacaccgtc ggtctcatct tccactcctt cctcctcgtc ccttacttct   2160
cctggaagta cagtcatcga cgccaccatt ccaacactgg ctccctcgag agagacgaag   2220
tgtttgtccc caagaagaag tcagacatca agtggtacgg caagtacctc aacaacccct   2280
tgggacgcac cgtgatgtta acggttcagt tcactctcgg ctggcctttg tacttagcct   2340
tcaacgtctc gggaagacct tacgacggcg gcttcgcttg ccatttccac cctaacgctc   2400
ccatctacaa cgaccgcgag cgtctccaga tatacatctc cgacgctggc atcctcgccg   2460
tctgctacgt tctctaccgc tacgctgctg tccaaggagt tgcctcgatg gtctgcttct   2520
acggagtccc gcttctgata gtcaacgggt tcttagtttt gatcacttac ttgcagcaca   2580
cgcatccttc cctgcctcac tacgattcgt ctgagtggga ttggttgagg ggagcgttgg   2640
ctaccgttga cagagactac gggatcttga acaaggtctt ccacaatatc acggacacgc   2700
acgtggcgca tcacctgttc tcgaccatgc cgcattatca cgcgatggaa gctaccaagg   2760
cgataaagcc gatactggga gagtattatc agttcgatgg gacgccggtg gttaaggcga   2820
tgtggaggga ggcgaaggag tgtatctatg tggaaccgga caggcaaggt gagaagaaag   2880
gtgtgttctg gtacaacaat aagttatga                                    2909
```

<210> SEQ ID NO 2
<211> LENGTH: 2909
<212> TYPE: DNA
<213> ORGANISM: Brassica juncea

<400> SEQUENCE: 2

```
gatattttt taagtttttt tctcacatgg gagaagaaga agccaagcac gatcctccat     60
tctcaacttt atagcatttt tttcttttct ttccggctac cactaacttc tacagttcta    120
cttgtgagtc ggcaaggacg tttcctcata ttaaagtaaa gacatcaaat accataatct    180
taatgctaat taacgtaacg gatgagttct ataacacaac ccaaactagt ctttgtgaac    240
attaggattg ggtaaaccaa tatttacatt ttaaaaacaa atacaaaaaa gaaacgtgat    300
aaactttata aaagcaatta tatgatcacg gcatcttttt cacttttccg taaatatata    360
taagtggtgt aaatatcaga tatttggagt agaaaaaaaa aaaaaaaaaa agaaatatga    420
agagaggaaa taatggaggg gcccactagt aaaaagaaa gaaaagagat gtcactcaat     480
cgtctcacac gggcccccgt caatttaaac ggcctgcctt ctgcccaatc gcatcttacc    540
agaaccagag agattcatta ccaaagagat agagagagaa agagaggaga cagagagagt    600
ttgaggaggt gcttcttcgt agggttcatc gttattaacg ttaaatcttc atcccctac     660
gtcaaccagc tcaaggtccc tttcttcttc catttcctct catttttacg ttgttttcaa    720
tcttggtctg ttcttttctt atcgcttttc tattctatct atcattttg cttttcagtc     780
gatttaattc tagacctgtt aatatttatt gcattaaact atagatctgt tcttgattct    840
ctgttttctt gtgtgaaatc ttgatgctgt ctttaccatt aatctgatta tattgtctat    900
accttggaga atatgaaatg ttgcattttc atttgtccga atacaaactg tttgactttc    960
aatcttttt aatgatttat tttgatgggt tggtggagtt gaaaaatcac catagcagtc   1020
tcacgtcctg gtcttagaaa tatccttcct attcaaagtt atatatattt gtttacttgt   1080
cttagatctg gacctgagac atgtaagtac ctatttgttg aatctttggg taaaaaactt   1140
atgtctctgg gtaaaatttg cttggagatt tgaccgattc ctattggctc ttgattctgt   1200
aattacgtaa tacatgaaaa atgtttcatt tggcctatgc tcacttcatg cttataaact   1260
```

-continued

```
ttttcttgca aattaattgg attagatgct ccttcataga ttcagatgca atagatttgc    1320
atgaagaaaa taatagaatt catgatagta aaaagattgt atttttgttt gtttgtttat    1380
gtttaaaagt ctatatgttg acaatagagt tgctatcaac tgtttcattt aggtttatgt    1440
ttttgtcaag ttgcttattc taagagacat tgtgattatg acttgtcttc tctaacgtag    1500
tttagtaata aaagacgaaa gaaattgata tccacaagaa agagatgtaa gctgtaacgt    1560
atcaaatctc attaataact agtagtattc tcaacgctat cgtttatttc tttcttggt     1620 ttgccactat atgccgcttc tctcctcttt tgtcccacgt actatccatt tttttgaaac    1680
tttaataacg taacactgaa tattaatttg ttggtttaat taactttgag tttgtttttg    1740
gtttatgcag aaacatgggt gcaggtggaa gaatgcaagt gtctcctccc tcgaagaagt    1800
ctgaaaccga caccatcaag cgcgtaccct gcgagacacc gcccttcact gtcggagaac    1860
tcaagaaagc aatcccaccg cactgtttca aacgctcgat ccctcgctct ttctcctacc    1920
tcatctggga catcatcata gcctcctgct tctactacgt cgccaccact tacttccctc    1980
tcctccctca ccctctctcc tacttcgcct ggcctctcta ctgggcctgc aggactgcg     2040 tcctaaccgg cgtctgggtc atagcccacg agtgcggcca ccacgccttc agcgactacc    2100
agtggcttga cgacaccgtc ggtctcatct tccactcctt cctcctcgtc ccttacttct    2160
cctggaagta cagtcatcga cgccaccatt ccaacactgg ctccctcgag agagacgaag    2220
tgtttgtccc caagaagaag tcagacatca agtggtacgg caagtacctc aacaaccctt    2280
tgggacgcac cgtgatgtta acggttcagt tcactctcgg ctggcctttg tacttagcct    2340
tcaacgtctc gggaagacct tacgacggcg gcttcgcttg ccatttccac cctaacgctc    2400
ccatctacaa cgaccgcgag cgtctccaga tatacatctc cgacgctggc atcctcgccg    2460
tctgctacgg tctctaccgc tacgctgctg tccaaggagt tgcctcgatg gtctgcttct    2520
acggagtccc gcttctgata gtcaacgggt tcttagtttt gatcacttac ttgcagcaca    2580
cgcatccttc cctgcctcac tacgattcgt ctgagtggga ttggttgagg ggagcgttgg    2640
ctaccgttga cagagactac gggatcttga acaaggtctt ccacaatatc acggacacgc    2700
acgtggcgca tcacctgttc tcgaccatgc cgcattatca cgcgatggaa gctaccaagg    2760
cgataaagcc gatactggga gagtattatc agttcgatgg gacgccggtg gttaaggcga    2820
tgtggaggga ggcgaaggag tgtatctatg tggaaccgga caggcaaggt gagaagaaag    2880
gtgtgttctg gtacaacaat aagttatga                                     2909
```

<210> SEQ ID NO 3
<211> LENGTH: 2909
<212> TYPE: DNA
<213> ORGANISM: Brassica juncea

<400> SEQUENCE: 3

```
gatatttttt taagtttttt tctcacatgg gagaagaaga agccaagcac gatcctccat      60
tctcaacttt atagcatttt tttctttct ttccggctac cactaacttc tacagttcta     120
cttgtgagtc ggcaaggacg tttcctcata ttaaagtaaa gacatcaaat accataatct     180
taatgctaat taacgtaacg gatgagttct ataacacaac ccaaactagt ctttgtgaac     240
attaggattg ggtaaaccaa tatttacatt ttaaaaacaa aatacaaaaa gaaacgtgat     300 aaacttatata aaagcaatta tatgatcacg gcatcttttt cacttttccg taaatatata    360
taagtggtgt aaatatcaga tatttggagt agaaaaaaaa aaaaaaaaaa agaaatatga    420
agagaggaaa taatggaggg gcccactagt aaaaaagaaa gaaagagat gtcactcaat     480
```

```
cgtctcacac gggcccccgt caatttaaac ggcctgcctt ctgcccaatc gcatcttacc    540
agaaccagag agattcatta ccaaagagat agagagagaa agagaggaga cagagagagt    600
ttgaggaggt gcttcttcgt agggttcatc gttattaacg ttaaatcttc atcccctac    660 gtcaaccagc tcaaggtccc tttcttcttc catttcctct cattttacg ttgttttcaa    720 tcttggtctg ttcttttctt atcgcttttc tattctatct atcattttg cttttcagtc    780 gatttaattc tagacctgtt aatatttatt gcattaaact atagatctgt tcttgattct    840
ctgttttctt gtgtgaaatc ttgatgctgt ctttaccatt aatctgatta tattgtctat    900
accttggaga atatgaaatg ttgcattttc atttgtccga atacaaactg tttgactttc    960
aatctttttt aatgatttat tttgatgggt tggtggagtt gaaaaatcac catagcagtc   1020
tcacgtcctg gtcttagaaa tatccttcct attcaaagtt atatatattt gtttacttgt   1080
cttagatctg gacctgagac atgtaagtac ctatttgttg aatctttggg taaaaaactt   1140
atgtctctgg gtaaaatttg cttggagatt tgaccgattc ctattggctc ttgattctgt   1200
aattacgtaa tacatgaaaa atgtttcatt tggcctatgc tcacttcatg cttataaact   1260
ttttcttgca aattaattgg attagatgct ccttcataga ttcagatgca atagatttgc   1320
atgaagaaaa taatagaatt catgatagta aaaagattgt attttgtttt gtttgtttat   1380
gtttaaaagt ctatatgttg acaatagagt tgctatcaac tgtttcattt aggtttatgt   1440
ttttgtcaag ttgcttattc taagagacat tgtgattatg acttgtcttc tctaacgtag   1500
tttagtaata aaagacgaaa gaaattgata tccacaagaa agagatgtaa gctgtaacgt   1560
atcaaatctc attaataact agtagtattc tcaacgctat cgtttatttc tttctttggt   1620
ttgccactat atgccgcttc tctcctcttt tgtcccacgt actatccatt tttttgaaac   1680
tttaataacg taacactgaa tattaatttg ttggtttaat taactttgag tttgtttttg   1740
gtttatgcag aaacatgggt gcaggtggaa gaatgcaagt gtctcctccc tcgaagaagt   1800
ctgaaaccga caccatcaag cgcgtaccct gcgagacacc gcccttcact gtcggagaac   1860
tcaagaaagc aatcccaccg cactgtttca aacgctcgat ccctcgctct ttctcctacc   1920
tcatctggga catcatcata gcctcctgct tctactacgt cgccaccact tacttccctc   1980
tcctccctca ccctctctcc tacttcgcct ggcctctcta ctgggcctgc cagggctgcg   2040
tcctaaccgg cgtctgggtc atagcccacg agtgcggcca ccacgccttc agcgactacc   2100
agtggcttga cgacaccgtc ggtctcatct tccactcctt cctcctcgtc ccttacttct   2160 cctgaagta cagtcatcga cgccaccatt ccaacactgg ctccctcgag agagacgaag   2220 tgttttgtccc caagaagaag tcagacatca agtggtacgg caagtacctc aacaacccttt   2280 tgggacgcac cgtgatgtta acggttcagt tcactctcgg ctggcctttg tacttagcct   2340
tcaacgtctc gggaagacct tacgacggcg gcttcgcttg ccatttccac cctaacgctc   2400
tcatctacaa cgaccgcgag cgtctccaga tatacatctc cgacgctggc atcctcgccg   2460
tctgctacgg tctctaccgc tacgctgctg tccaaggagt tgcctcgatg gtctgcttct   2520
acggagtccc gcttctgata gtcaacgggt tcttagtttt gatcacttac ttgcagcaca   2580
cgcatccttc cctgcctcac tacgattcgt ctgagtggga ttggttgagg ggagcgttgg   2640
ctaccgttga cagagactac gggatcttga acaaggtctt ccacaatatc acggacacgc   2700
acgtggcgca tcacctgttc tcgaccatgc cgcattatca cgcgatggaa gctaccaagg   2760
cgataaagcc gatactggga gagtattatc agttcgatgg gacgccggtg gttaaggcga   2820
tgtggaggga ggcgaaggag tgtatctatg tggaaccgga caggcaaggt gagaagaaag   2880
```
gtgtgttctg gtacaacaat aagttatga                                    2909

<210> SEQ ID NO 4
<211> LENGTH: 384
<212> TYPE: PRT
<213> ORGANISM: Brassica juncea

<400> SEQUENCE: 4

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
        50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu
```

```
                    370             375             380
```

<210> SEQ ID NO 5
<211> LENGTH: 384
<212> TYPE: PRT
<213> ORGANISM: Brassica juncea

<400> SEQUENCE: 5

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
                20                  25                  30

Val Gly Glu Leu Lys Lys Ala Ile Pro Pro His Cys Phe Lys Arg Ser
                35                  40                  45

Ile Pro Arg Ser Phe Ser Tyr Leu Ile Trp Asp Ile Ile Ala Ser
            50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Asp Cys Val
                    85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Phe His Ser
                115                 120                 125

Phe Leu Leu Val Pro Tyr Phe Ser Trp Lys Tyr Ser His Arg Arg His
            130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
                180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
                260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
```

370             375             380

<210> SEQ ID NO 6
<211> LENGTH: 384
<212> TYPE: PRT
<213> ORGANISM: Brassica juncea

<400> SEQUENCE: 6

Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65              70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Asp Gly Gly Phe Ala
        195                 200                 205

Cys His Phe His Pro Asn Ala Leu Ile Tyr Asn Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
        355                 360                 365

Asp Arg Gln Gly Glu Lys Lys Gly Val Phe Trp Tyr Asn Asn Lys Leu

<210> SEQ ID NO 7
<211> LENGTH: 383
<212> TYPE: PRT
<213> ORGANISM: Brassica juncea

<400> SEQUENCE: 7

Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
                20                  25                  30

Val Gly Glu Leu Lys Lys Ala Ile Pro Pro His Cys Phe Lys Arg Ser
                35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Val Ile Ala His Glu Cys Gly His His Ala Phe Ser
                100                 105                 110

Asp Tyr Gln Trp Leu Asp Asp Thr Val Gly Leu Ile Phe His Ser Phe
                115                 120                 125

Leu Leu Val Pro Tyr Phe Ser Trp Lys Tyr Ser His Arg Arg His His
    130                 135                 140

Ser Asn Thr Gly Ser Leu Glu Arg Asp Glu Val Phe Val Pro Lys Lys
145                 150                 155                 160

Lys Ser Asp Ile Lys Trp Tyr Gly Lys Tyr Leu Asn Asn Pro Leu Gly
                165                 170                 175

Arg Thr Val Met Leu Thr Val Gln Phe Thr Leu Gly Trp Pro Leu Tyr
                180                 185                 190

Leu Ala Phe Asn Val Ser Gly Arg Pro Tyr Asp Gly Gly Phe Ala Cys
                195                 200                 205

His Phe His Pro Asn Ala Pro Ile Tyr Asn Asp Arg Glu Arg Leu Gln
    210                 215                 220

Ile Tyr Ile Ser Asp Ala Gly Ile Leu Ala Val Cys Tyr Gly Leu Tyr
225                 230                 235                 240

Arg Tyr Ala Ala Val Gln Gly Val Ala Ser Met Val Cys Phe Tyr Gly
                245                 250                 255

Val Pro Leu Leu Ile Val Asn Gly Phe Leu Val Leu Ile Thr Tyr Leu
                260                 265                 270

Gln His Thr His Pro Ser Leu Pro His Tyr Asp Ser Ser Glu Trp Asp
                275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Gln Phe Asp Gly Thr Pro Val Val
                340                 345                 350

Lys Ala Met Trp Arg Glu Ala Lys Glu Cys Ile Tyr Val Glu Pro Asp
                355                 360                 365

Arg Gln Gly Glu Lys Lys Gly Val Phe Trp Tyr Asn Asn Lys Leu

-continued

```
<210> SEQ ID NO 8
<211> LENGTH: 23
<212> TYPE: DNA
<213> ORGANISM: Artificial
<220> FEATURE:
<223> OTHER INFORMATION: FAD2Pup-1 primer

<400> SEQUENCE: 8
gaagccaagc acgatcctcc att                                              23

<210> SEQ ID NO 9
<211> LENGTH: 23
<212> TYPE: DNA
<213> ORGANISM: Artificial
<220> FEATURE:
<223> OTHER INFORMATION: 2BR4 primer

<400> SEQUENCE: 9
acacgcttga gggtatcggt ttc                                              23

<210> SEQ ID NO 10
<211> LENGTH: 22
<212> TYPE: DNA
<213> ORGANISM: Artificial
<220> FEATURE:
<223> OTHER INFORMATION: FAD2low primer

<400> SEQUENCE: 10
tcataactta ttgttgtacc ag                                               22
```